US010034899B2

(12) United States Patent
Kessler et al.

(10) Patent No.: US 10,034,899 B2
(45) Date of Patent: Jul. 31, 2018

(54) SOLID ORAL DOSAGE FORM FOR BREAST SYMPTOMS

(71) Applicant: BioPharmX, Inc., Menlo Park, CA (US)

(72) Inventors: Jack Kessler, Southborough, MA (US); Robert Kehl Sink, Sunnyvale, CA (US)

(73) Assignee: BioPharmX, Inc., Menlo Park, CA (US)

( * ) Notice: Subject to any disclaimer, the term of this patent is extended or adjusted under 35 U.S.C. 154(b) by 0 days.

(21) Appl. No.: 14/550,915

(22) Filed: Nov. 22, 2014

(65) Prior Publication Data

US 2015/0147400 A1 May 28, 2015

Related U.S. Application Data

(60) Provisional application No. 61/909,838, filed on Nov. 27, 2013.

(51) Int. Cl.

| | |
|---|---|
| *A61K 33/18* | (2006.01) |
| *A61K 33/06* | (2006.01) |
| *A61K 9/50* | (2006.01) |
| *A61K 31/59* | (2006.01) |
| *A61K 33/04* | (2006.01) |
| *A61K 33/26* | (2006.01) |
| *A61K 31/07* | (2006.01) |
| *A61K 31/202* | (2006.01) |
| *A61K 31/51* | (2006.01) |
| *A61K 31/592* | (2006.01) |
| *A61K 31/593* | (2006.01) |
| *A61K 33/30* | (2006.01) |

(52) U.S. Cl.
CPC ............ *A61K 33/18* (2013.01); *A61K 9/5084* (2013.01); *A61K 31/07* (2013.01); *A61K 31/202* (2013.01); *A61K 31/51* (2013.01); *A61K 31/59* (2013.01); *A61K 31/592* (2013.01); *A61K 31/593* (2013.01); *A61K 33/04* (2013.01); *A61K 33/06* (2013.01); *A61K 33/26* (2013.01); *A61K 33/30* (2013.01)

(58) Field of Classification Search
None
See application file for complete search history.

(56) References Cited

U.S. PATENT DOCUMENTS

| | | |
|---|---|---|
| 1,841,694 A | 1/1932 | Amend et al. |
| 4,113,857 A | 9/1978 | Shetty |
| 4,338,304 A | 7/1982 | Kamimae et al. |
| 4,816,255 A | 3/1989 | Ghent et al. |
| 4,954,351 A | 9/1990 | Sackler et al. |
| 5,232,914 A | 8/1993 | Fellman |
| 5,250,304 A | 10/1993 | Ghent et al. |
| 5,589,198 A | 12/1996 | Ghent et al. |
| 5,885,592 A * | 3/1999 | Duan ............... A61K 9/2009 424/400 |
| 5,910,318 A | 6/1999 | Ghent et al. |
| 5,955,101 A | 9/1999 | Ghent et al. |
| 6,019,970 A | 2/2000 | Ghent et al. |
| 6,248,335 B1 | 6/2001 | Duan et al. |
| 6,566,382 B2 | 5/2003 | Still et al. |
| 6,592,890 B1 | 7/2003 | Green |
| 6,953,588 B2 * | 10/2005 | Cooper ............... A61K 31/01 424/400 |
| 8,440,252 B2 * | 5/2013 | Ghosh ............... A23L 27/40 426/645 |
| 8,486,375 B2 | 7/2013 | Tamarkin et al. |
| 2001/0008497 A1 | 7/2001 | Horiguchi et al. |
| 2002/0187205 A1 | 12/2002 | Paradissis |
| 2003/0194447 A1 | 10/2003 | Scholz et al. |
| 2006/0034944 A1 | 2/2006 | Rushlow et al. |
| 2006/0177511 A1 | 8/2006 | Scholz et al. |
| 2006/0251722 A1 * | 11/2006 | Bandak ............... A61K 9/2081 424/472 |

(Continued)

FOREIGN PATENT DOCUMENTS

| | | |
|---|---|---|
| EP | 1044689 A1 | 10/2000 |
| WO | WO 1997/031643 A1 | 9/1997 |

(Continued)

OTHER PUBLICATIONS

Raileanu et al. "Vitamin A stability in salt triple fortified with iodine, iron, and vitamin A." Fod and Nutrition Bulletin, vol. 27, No. 3 2006 pp. 252-259.*
Notification of Transmittal of International Search Report and Written Opinion of the International Searching Authority, or the Declaration for PCT application PCT/US2014/066979, dated Feb. 23, 2015.
International Search Report and Written Opinion of the International Searching Authority for International Patent Application No. PCT/2017/028995 dated Jun. 27, 2017.
Taurog et al., "Conversion of iodate to iodide in vivo and in vitro", J. Biol. Chem., vol. 241, No. 20, pp. 4684-4693 (1966).

*Primary Examiner* — Robert A Wax
*Assistant Examiner* — Danah Al-Awadi
(74) *Attorney, Agent, or Firm* — Robert Kehl Sink; McDermott Will & Emery LLP

(57) ABSTRACT

The invention is a solid oral dosage form that is designed to deliver a supraphysiological dose of molecular iodine of 3 to 60 mg per day. The solid oral dosage form is designed to have a low risk of thyroid related adverse clinical events for patients with deficiencies of certain minerals. The solid oral dosage form includes a source of iodine, a reactive agent, and calcium or iron. The solid oral dosage form may include one or more of selenium, vitamin A, vitamin D, zinc, gamma-linolenic acid, vitamin B1, and magnesium. The solid dosage form may further comprise an enteric coating that coats ingredients that are absorbed predominantly from the intestines, such as vitamin A and D, and does not coat the source of iodine and the reactive agent.

44 Claims, 2 Drawing Sheets

(56) References Cited

U.S. PATENT DOCUMENTS

2007/0059378 A1*  3/2007  Bland .................... A61K 31/07
                                                        424/601
2008/0193531 A1    8/2008  Hermelin et al.
2009/0017139 A1    1/2009  Kessler
2009/0047218 A1    2/2009  Hansjorg
2012/0015046 A9    1/2012  Giordano et al.
2015/0147400 A1    5/2015  Kessler et al.

FOREIGN PATENT DOCUMENTS

| WO | WO 2001/028600 A1 | 4/2001 |
| WO | WO 2003/047605 A1 | 6/2003 |
| WO | WO 2005/115472 A2 | 12/2005 |
| WO | WO 2006/067798 A1 | 6/2006 |
| WO | WO 2009/087647 A1 | 7/2009 |
| WO | WO 2012/002943 A1 | 1/2012 |

* cited by examiner

SOLID ORAL DOSAGE FORM FOR BREAST SYMPTOMS

CROSS-REFERENCE TO RELATED APPLICATIONS

This application claims the benefit of priority to U.S. Provisional Application No. 61/909,838 filed Nov. 27, 2013 the contents of which is incorporated herein by reference in its entirety.

FIELD

This disclosure relates generally to a solid oral dosage form comprising a deliverable form of iodine for treating symptoms related to fibrocystic breast condition and for prophylactically maintaining breast health in pre-menopausal women, along with related methods for making and administering such dosage form. More particularly, this disclosure relates to a solid oral dosage form that (1) is effective to deliver supraphysiological levels of molecular iodine, and (2) provides beneficial supporting ingredients directed to reducing thyroid-related adverse events upon oral administration, among other features.

BACKGROUND

Fibrocystic breast condition, also referred to as mammary dysplasia, benign breast condition, and diffuse cystic mastopathy, is a benign condition, generally in pre-menopausal women, characterized by the presence of lumps or cysts in the breasts. The condition is fairly common; approximately 60% of women are estimated to have experienced fibrocystic breast condition at some point in their lives. The condition may, for example, be accompanied by pain or discomfort in one or both breasts, tenderness, swelling, breast thickness. The condition can cause extreme discomfort, and can also make the detection of breast cancer more difficult.

The specific cause of fibrocystic breast condition and accompanying changes in the breasts isn't fully understood, although it is believed that estrogen and other reproductive hormones play a role. The occurrence of symptoms may be cyclical or non-cyclical (many women experience symptoms just prior to menstruation). Commonly recommended treatments include administration of over-the-counter pain relievers such as ibuprofen or acetaminophen, application of warm or cold compresses, administration of estrogen or other hormones, fine-needle aspiration for removing fluid from fluid-filled cysts or surgical removal if warranted, and modification of diet. Additional alternative approaches have been suggested for relieving the symptoms of fibrocystic breast condition including the implementation of a vegetarian diet, limiting the intake of caffeine, implementing a low-fat diet, and intake of dietary supplements and herbal remedies such as dandelion leaf, cleavers, and yarrow. Topical approaches include the application of poke root oil or a gel or cream of natural progesterone to the breasts. At present, there does not appear to be consensus amongst the members of the medical community regarding effective therapies for treating fibrocystic breast condition.

One supplement that has been suggested for treating fibrocystic breast condition, among other conditions, is iodine. The use of iodine is complicated by its administration in many different forms. Iodine may be delivered as organically-bound iodine (e.g., caseinated iodine), inorganic iodine, and molecular iodine, i.e., $I_2$; each of these forms of iodine has been used to treat conditions in addition to fibrocystic breast condition such as iodine deficiency, goiter, hypothyroidism, etc. Some ingestible iodine compositions include iodide salts having no mechanism for efficient conversion of iodide to molecular iodine prior to absorption into internal tissue. Other compositions include an unstable form of molecular iodine that reacts to form iodide salts prior to significant interaction with internal tissue. Examples of iodide salts include potassium iodide and sodium iodide, both of which are used in iodized salt in many countries. Iodide (CAS Registry Number: 20461-54-5) and molecular iodine (CAS Registry Number: 7553-56-2) differ significantly in their chemical nature and physiologic interactions with the human body. Iodide (typically administered with a suitable counter-ion) has an anionic charge and is hydrophilic, stable in water, and is also highly water soluble, whereas in contrast, molecular iodine is uncharged and hydrophobic, and reacts rapidly with water, making it unstable at pH values above 6.0.

Significant differences also exist between iodide and molecular iodine in terms of the toxicity and therapeutic efficacy of orally administered forms thereof (K. D. Thrall, Ph.D. dissertation, Washington State University, Program in Pharmacology and Toxicology, December 1990). Despite the differences in pharmacologic and toxicological activity between molecular iodine and iodide as noted above, the term "iodine" is frequently used interchangeably to refer to these two species, as well as to several other distinct chemical species that contain iodine atoms. Iodide salts are frequently simply described as iodine due to the fact that the iodide salts contain ionic forms of atomic iodine. Much of the prior art, including the scientific medical literature, uses the term "iodine" somewhat imprecisely in this regard.

Human consumption of iodide at levels of 0.150 to 1.1 mg per day has been established as safe for the general population by FDA researchers (J. A. Pennington, "A review of iodine toxicity reports," *J. Am. Dietetic Assoc.*, Vol. 90, Number 11, pp. 1571-1581 1990). Above this level, the primary safety concern is the thyroid organ. There are discrete patient populations that have an elevated risk of experiencing thyroid-related adverse events when exposed to daily supraphysiological iodine above the levels described above.

In a Phase II clinical study, dosing with a molecular iodine-based dosage form as described in U.S. Pat. Nos. 5,885,592 and 6,248,335 was demonstrated as a safe and effective treatment for treating symptoms related to fibrocystic breast condition. However, there remains a need for dosage forms and related therapies for treatment of fibrocystic breast condition that can deliver supraphysiological doses of iodine in an amount effective to result in a notable reduction in one or more symptoms associated with fibrocystic breast condition, and that are effective and safe for rapidly establishing normal thyroid function in those individuals who are deficient in key nutritional cofactors.

SUMMARY

The present disclosure overcomes certain limitations of the prior art by providing a solid oral dosage form comprising a deliverable source of iodine in a therapeutically effective amount. In a first aspect, the solid oral dosage form comprises a source of iodine, a reactive agent capable of reaction with the source of iodine, and a metal ion selected from calcium or iron. Generally, the iodine source is unreactive (i.e., stable and does not substantially react with the reactive agent) when the solid oral dosage form is maintained under normal storage conditions. Following ingestion of the solid dosage form and upon exposure to the gastric environment (gastric juices of the stomach), the source of iodine reacts with the reactive agent to generate molecular iodine in-vivo. For example, when the solid oral dosage form is added to simulated gastric fluid and maintained therein for a suitable period of up to 2 hours, the source of iodine reacts with the reactive agent to generate molecular iodine in-situ, generally in a ratio of molecular iodine to total iodine in the range of 0.8 to 1.0 by weight. Preferably, generation of molecular iodine in-situ upon exposure to simulated gastric fluid at the foregoing ratio occurs within an exposure period of from 1 to 60 minutes, or more preferably, within a period of 60 minutes. The total iodine content of the solid oral dosage (to be described in greater detail infra) form ranges from 3 milligrams (mg) to 60 milligrams.

In some embodiments, the total iodine content in the solid dosage form is selected from the following: from greater than 6 milligrams to 60 milligrams, from greater than 6 milligrams to 50 milligrams, or from greater than 6 milligrams to 40 milligrams.

In some embodiments, the total iodine content in the dosage form is selected from the following: from 7 milligrams to 50 milligrams, from 8 milligrams to 40 milligrams, from 9 milligrams to 30 milligrams, from 9 milligrams to 25 milligrams, and from 10 milligrams to 25 milligrams.

In some embodiments, the reaction between the source of iodine and the reactive agent that occurs in a gastric environment (i.e., in simulated gastric fluid) is an oxidation-reduction reaction. For example in some embodiments, the source of iodine and the reactive agent comprise an iodide salt (e.g., potassium iodide) and an iodate salt (e.g. potassium iodate), and the reaction which occurs in a gastric environment is an oxidation-reduction.

In some embodiments, the solid oral dosage form further comprises a pH control agent (e.g., a buffer) such that the effective pH of the solid oral dosage form is between 7.0 and 12.0. In some embodiments, the effective pH of the solid oral dosage form is between 8.0 and 12.0. In some embodiments, the effective pH of the solid oral dosage form is between 9.0 and 12.0.

In yet additional embodiments of the solid oral dosage form, the ratio of the source of iodine to the reactive agent is within ±20% of a ratio effective to result in a ratio of molecular iodine to total iodine within the range 0.95 to 1.0. For example, in a solid oral dosage form comprising an iodide salt and an iodate salt, the ideal ratio of iodide (I$^-$) to iodate (IO$_3^-$) is 5:1, where ±20% of this idealized ratio corresponds to a range of 4:1 to 6:1.

In some embodiments, the metal ion is calcium and the solid oral dosage form further comprises vitamin A.

In some embodiments, the vitamin A comprised within the solid oral dosage is enterically coated.

In some embodiments, the metal ion is iron and the solid oral dosage form further comprises vitamin D. In some embodiments, the vitamin D comprised within the solid dosage form is enterically coated.

In some additional embodiments, the solid oral dosage form comprises a source of iodine, a reactive agent capable of reaction with the source of iodine, a metal ion that is calcium and/or iron, and further comprises selenium.

In some further embodiments, the solid oral dosage form comprises as its metal ion components selenium and iron.

In some embodiments, the solid oral dosage form comprises in addition to its iodine-generating components, the metal ions selenium, calcium and iron, and as its vitamin components, vitamin A and vitamin D, which may optionally be enterically coated. The vitamin components may be individually enterically coated or may comprise a mixture which is enterically coated.

In some embodiments, the solid oral dosage form further comprises one or more ingredients selected from the group consisting of GLA (gamma-linolenic acid), vitamin B1, magnesium, and zinc.

In some embodiments, the solid oral dosage form is absent selenium.

In some embodiments, the solid oral dosage form is absent GLA (gamma-linolenic acid).

In some embodiments, the solid oral dosage form comprises a source of iodine, a reactive agent capable of reaction with the source of iodine (as described above), iron, and selenium. The source of iodine is unreactive within the dosage form when maintained under normal storage conditions. Upon exposure of solid oral dosage form to stomach acid or simulated gastric fluid, the source of iodine reacts with the reactive agent to generate molecular iodine in a ratio of molecular iodine to total iodine in the range of 0.8 to 1.0 by weight. In some embodiments of the foregoing, the solid oral dosage form further comprises vitamin A, where the vitamin A is enterically-coated. The enteric coating coats the vitamin A and does not coat at least a portion of both the source of iodine and the reactive agent. The total iodine content of the solid oral dosage form is generally from 3 to 60 mg, such as from 6 to 50 mg. The amount of iron, selenium, and vitamin A in the solid oral dosage form is 0.5 to 20 mg, 25 to 100 micrograms (μg), and 10 to 1000 μg, respectively. In preferred embodiments, the amount of iron, selenium, and vitamin A in the solid oral dosage form is 0.5 to 10 mg, 40 to 100 μg, and 10 to 500 μg, respectively.

In yet one or more additional embodiments, the solid oral dosage form comprises a source of iodine, a reactive agent capable of reaction with the source of iodine, calcium, and selenium. The source of iodine is unreactive when the solid oral dosage form is maintained under normal storage conditions. However, when the solid oral dosage form is added to stomach acid or simulated gastric fluid, the source of iodine reacts with the reactive agent to generate molecular iodine in a ratio of molecular iodine to total iodine in the range of 0.8 to 1.0 by weight. This embodiment may further comprise vitamin D and an enteric coating. In such an embodiment, the enteric coating coats the vitamin D and does not coat at least a portion of both the source of iodine and the reactive agent. The total iodine content of the solid oral dosage form is 3 to 60 mg, such as from 6 to 50 mg. The amount of calcium, selenium, and vitamin D in the solid oral dosage form is 10 to 500 mg, 25 to 100 μg, and 1 to 30 μg, respectively. In preferred embodiments, the amount of calcium, selenium, and vitamin D in the solid oral dosage form is 10 to 200 mg, 40 to 100 μg, and 1 to 10 μg, respectively.

In one or more embodiments, the solid oral dosage form comprises a source of iodine, a reactive agent capable of reaction with the source of iodine, calcium, iron, and selenium. The source of iodine is unreactive when the solid oral dosage form is maintained under normal storage conditions. However, when the solid oral dosage form is added to simulated gastric fluid, the source of iodine reacts with the reactive agent to generate molecular iodine in a ratio of molecular iodine to total iodine in the range of 0.8 to 1.0 by weight. This embodiment may further comprise vitamins A and D and an enteric coating. In such an embodiment, the enteric coating coats the vitamins A and D and does not coat at least a portion of both the source of iodine and the reactive agent. The total iodine content of the solid oral dosage form is 3 to 60 mg. In some embodiments of the foregoing, the total iodine content is selected from the following: from greater than 6 milligrams to 60 milligrams, from greater than 6 milligrams to 50 milligrams, or from greater than 6 milligrams to 40 milligrams. In some embodiments, the total iodine content in the dosage form is selected from the following: from 7 milligrams to 50 milligrams, from 8 milligrams to 40 milligrams, from 9 milligrams to 30 milligrams, from 9 milligrams to 25 milligrams, and from 10 milligrams to 25 milligrams.

The amount of iron, calcium, selenium, vitamin A, and vitamin D in the solid oral dosage form is 0.2 to 20 mg, 10 to 500 mg, 25 to 100 µg, 10 to 500 µg, and 1 to 30 µg, respectively. In some preferred embodiments, the amount of iron, calcium, selenium, vitamin A, and vitamin D in the solid oral dosage form is 0.2 to 5 mg, 10 to 200 mg, 40 to 100 µg, 10 to 200 µg, and 1 to 10 µg, respectively.

In some embodiments, the solid oral dosage form comprises a source of iodine, a reactive agent capable of reaction with the source of iodine and calcium. The solid oral dosage form is effective to generate molecular iodine when exposed to stomach acid or simulated gastric fluid as described previously. The total iodine content of the solid oral dosage form is as previously described. The amount of calcium in the solid oral dosage form ranges from 10 to 500 mg. In some preferred embodiments, the amount of calcium in the solid oral dosage form is from 10 mg to 200 mg or from 20 mg to 100 mg.

In some embodiments, the solid oral dosage form comprises a source of iodine, a reactive agent capable of reaction with the source of iodine and iron. The solid oral dosage form is effective to generate molecular iodine when exposed to stomach acid or simulated gastric fluid as described previously. The total iodine content of the solid oral dosage is as previously described. The amount of iron in the solid oral dosage form ranges from 0.2 mg to 20 mg. In some preferred embodiments, the amount of iron in the solid oral dosage form ranges from 0.2 mg to 5 mg, or from 5 mg to 20 mg.

In some embodiments, the solid oral dosage form comprises a source of iodine, a reactive agent capable of reaction with the source of iodine and further comprises the metal ions, iron or calcium, and at least one ingredient selected from GLA, vitamin B1, magnesium, and zinc. The source of iodine is unreactive when the solid oral dosage form is maintained under normal storage conditions. However, when the solid oral dosage form is exposed to stomach acid or simulated gastric fluid, the source of iodine reacts with the reactive agent to generate molecular iodine in a ratio of molecular iodine to total iodine in the range of 0.8 to 1.0 by weight. The total iodine content of the solid oral dosage form falls within a range of 3 mg to 60 mg. In some embodiments of the foregoing, the total iodine content is selected from the following: from greater than 6 milligrams to 60 milligrams, from greater than 6 milligrams to 50 milligrams, or from greater than 6 milligrams to 40 milligrams. In some embodiments, the total iodine content in the dosage form is selected from the following: from 7 milligrams to 50 milligrams, from 8 milligrams to 40 milligrams, from 9 milligrams to 30 milligrams, from 9 milligrams to 25 milligrams, and from 10 milligrams to 25 milligrams. The amount of iron or calcium in the solid oral dosage form is from 0.2 to 20 mg or from 10 mg to 500 mg, respectively. In some preferred embodiments, the amount of iron or calcium in the solid oral dosage form is from 0.2 to 5 mg, or from 10 mg to 200 mg, respectively. In one or more preferred embodiments, the amount of iron or calcium in the solid oral dosage form is from about 5 to 20 mg or from 20 to 100 mg, respectively.

The amount of GLA, vitamin B1, magnesium, or zinc is from 30 to 300 mg, from 1 to 100 mg, from 5 to 350 mg, or from 0.5 to 20 mg, respectively. In yet other preferred embodiments, the amount of GLA, vitamin B1, magnesium, or zinc is from 50 to 150 mg, from 1 to 10 mg, from 10 to 100 mg, or from 1 to 10 mg, respectively. In yet other preferred embodiments, the amount of GLA, vitamin B1, magnesium or zinc is from 50 to 150 mg, from 1 to 10 mg, from 20 to 50 mg, or from 1 to 4 mg, respectively. In some embodiments of the foregoing, the solid oral dosage form is absent GLA.

In a second aspect, a method of ingesting the solid oral dosage forms provided herein is provided for the treatment of fibrocystic breast condition. In one or more embodiments, ingesting the solid oral dosage forms described herein is effective to treat at least one of the symptoms of fibrocystic breast condition including cyclical breast pain, breast tenderness, and breast nodularity. Ingestion of the solid oral dosage form provided herein can extend for a period of at least 28 days, and preferably for at least 60 days. In some embodiments, the solid oral dosage form is taken on an empty stomach.

In one or more embodiments, the solid oral dosage form may further comprise vitamin A and/or vitamin D and an enteric coating. In some embodiments, the enteric coating coats the vitamin A and/or D and does not coat at least a portion of both the source of iodine and the reactive agent. The total iodine content of the solid oral dosage form is from about 3 to 60 mg. In some embodiments of the foregoing, the total iodine content is selected from the following: from greater than 6 milligrams to 60 milligrams, from greater than 6 milligrams to 50 milligrams, or from greater than 6 milligrams to 40 milligrams. In some embodiments, the total iodine content in the dosage form is selected from the following: from 7 milligrams to 50 milligrams, from 8 milligrams to 40 milligrams, from 9 milligrams to 30 milligrams, from 9 milligrams to 25 milligrams, and from 10 milligrams to 25 milligrams.

In some embodiments of the method, the amount of iron, calcium, selenium, vitamin A, and vitamin D in the solid oral dosage form is 0.2 to 20 mg, 10 to 500 mg, 25 to 100 µg, 10 to 1000 µg, and 1 to 30 µg, respectively, for those of the foregoing ingredients that are comprised in the solid dosage form. In some preferred embodiments, the amount of iron, calcium, selenium, vitamin A, and vitamin D in the solid oral dosage form is 0.2 to 5 mg, 10 to 200 mg, 40 to 100 µg, 10 to 500 µg, and 1 to 10 µg, respectively, for those of the foregoing ingredients that are comprised in the solid dosage form. In some preferred embodiments, the amount of iron, calcium, selenium, vitamin A, and vitamin D in the solid oral dosage form is 5 to 20 mg, 20 to 100 mg, 70 to 90 µg, 50 to 300 µg, and 2 to 5 µg, respectively, for those of the foregoing ingredients that are comprised therein.

In a third aspect, a method for fabricating a solid dosage form is provided. The method comprises the steps of combining (i) a source of iodine, (ii) a reactive agent capable of reaction with the source of iodine, and (iii) iron or calcium in a form suitable for administration to a mammalian subject, and fabricating a solid dosage form from the mixture of the combined ingredients, wherein the solid dosage form comprises (a) from about 0.2 to 20 mg iron or 10 to 500 mg of calcium and (b) 3 to 60 mg of total iodine, and wherein the source of iodine and the reactive agent react together to produce 2.4 to 60 mg of molecular iodine when the solid dosage form is placed in simulated gastric fluid for a period of up to 2 hours. In some preferred embodiments, the source of iron or calcium is selected from the corresponding salts listed in Table 1.

In one or more embodiments, the method may further comprise the step of including in the combining step one or more additional ingredients selected from the group consisting of selenium, vitamin A, vitamin D, GLA, vitamin B1, magnesium, and zinc. In some preferred embodiments, the sources of the additional ingredients are selected from the corresponding items listed in Table 1. In one or more embodiments, the method further comprises the step of including, in the combining step, an enterically coated form of the one or more added ingredients. In a preferred embodiment, the method comprises including in the combining step enterically coated vitamin A and/or enterically coated vitamin D. In some embodiments, the one or more additional ingredients included in the combining step is not selenium or GLA.

In one or more embodiments, the method further comprises the step of adding one or more additives or pharmaceutically acceptable excipients selected from the group consisting of a film former, a plasticizer, a binder, a lubricant, a colorant, an opaquant.

These and other objects and features of the invention will become more fully apparent when read in conjunction with the following detailed description.

DETAILED DESCRIPTION

Figure 1:
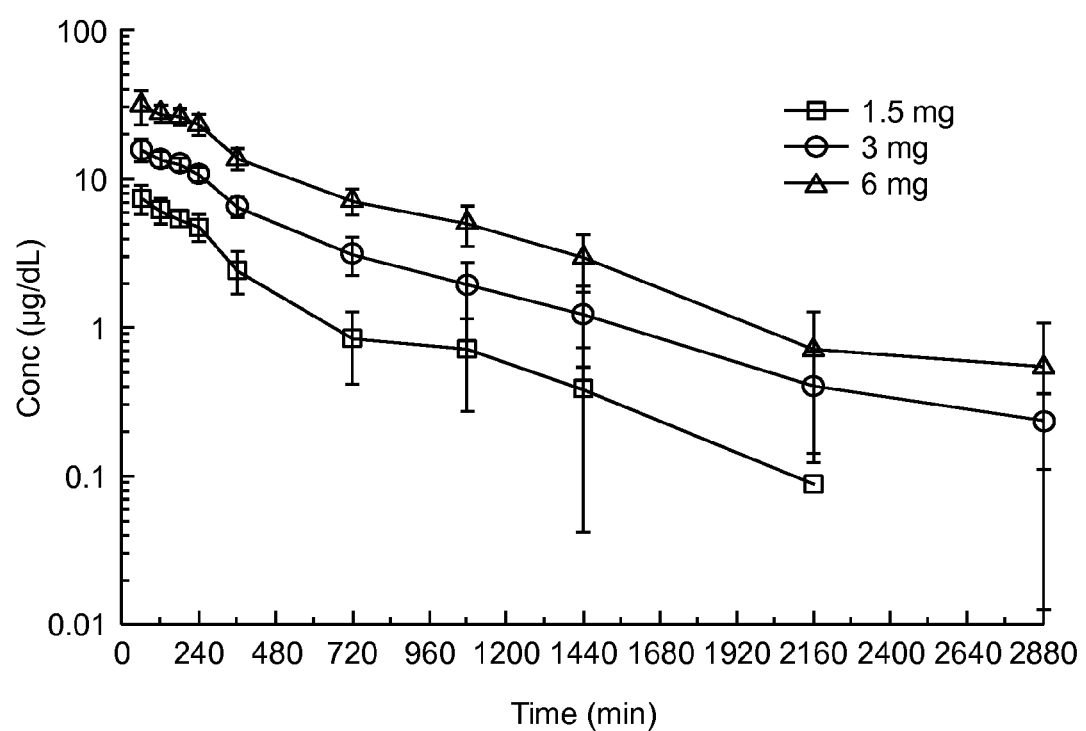
FIG. 1 is a graph of the change in mean total iodine concentration in serum after oral administration of 1.5, 3, and 6 milligram (mg) doses of molecular iodine to healthy female volunteers as described in Example 1. Measurements were made using an inductively coupled, plasma mass spectrometer. The mean total iodine values are plotted with the standard deviation for each population.

The present invention will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document which are incorporated herein by reference.

Definitions

It must be noted that, as used in this specification, the singular forms "a," "an," and "the" include plural referents unless the context clearly dictates otherwise. Thus, for example, reference to a "source of iodine" includes a single source as well as two or more different sources, reference to a "metal" refers to a single metal as well as to two or different metals, reference to an "excipient" includes a single excipient as well as two or more different excipients, and the like.

In describing and claiming the present invention, the following terminology will be used in accordance with the definitions described infra.

The term "solid oral dosage form" refers to a solid (i.e., non-fluid) dosage form that comprises pharmaceutically acceptable ingredients and is to be administered orally to an animal or human.

The term "molecular iodine" refers to diatomic iodine, which is represented by the chemical symbol $I_2$ (CAS Registry Number: 7553-56-2) whether in the liquid or solid state. The concentration of molecular iodine can be measured by the method described by Gottardi (Gottardi, W., Fresenius Z. *Anal. Chem.* Vol. 314, pp. 582-585, 1983).

The term "iodide" or "iodide anion" refers to the species which is represented by the chemical symbol $I^-$ (CAS Registry Number: 20461-54-5). Suitable counter-ions for the iodide anion include sodium, potassium, calcium, and the like.

The term "iodine" is used to refer to the element iodine in any form. Similarly, the term "source of iodine" refers to an entity that contains at least one iodine atom. Examples of sources of iodine include iodide anion per se, salts of iodide (e.g., potassium iodide, sodium iodide, and calcium iodide), molecular iodine, triiodide ($I_3^-$), organically complexed forms of iodine, covalently bound forms of iodine, iodate, and polyiodides. Examples of organically complexed forms of iodine include iodinated lipids, iodinated glycerol, iodinated triglycerides (e.g. triglycerides of oleic acid), iodinated fatty acid esters, and iodinated unsaturated fats.

The term "total iodine" in a sample refers to the amount of iodine, irrespective of form, from all iodine containing components within a sample. The concentration of total iodine can be measured by a thiosulfate titration as described in the United States Pharmacopeia (USP).

The term "ratio of molecular iodine to total iodine" in a sample refers to the ratio of the concentration by weight of iodine in all molecular iodine ($I_2$) in the sample divided by the concentration by weight of total iodine from all iodine containing components within the sample. The concentration of molecular iodine can be measured by a thiosulfate titration as described in the United States Pharmacopeia (USP).

The term "supraphysiologic" in relation to a chronic dosing of iodine refers to doses exceeding 1.1 mg per day of total iodine.

The term "stimulated gastric fluid" (SGF) is based on the USP Pharmacopeia and refers to a solution formed by dissolving 2.0 g of sodium chloride in 7.0 ml of hydrochloric acid and sufficient water to produce 1000 ml of solution. This solution has a pH of approximately 1.2.

The term "enteric coating" refers to a substance that forms a delayed release dosage form (as defined by U.S. Pharmacopeia <711>) for the ingredients mixed therein. A solid dosage form can be tested to determine whether its ingredients, such as vitamins A and/or D, are coated by an enteric coating by following the procedures described by Method A for delayed-release dosage forms in U.S. Pharmacopeia <711>.

The term "pharmaceutically acceptable" in reference to a formulation component or ingredient is one that may be included in the solid oral dosage forms/dosage forms provided herein and that causes no significant adverse toxicological effects in the patient at specified levels, or if levels are not specified, at levels known to be acceptable by those skilled in the art. All ingredients in the solid oral dosage forms described in this application are pharmaceutically acceptable. For clarity, molecular iodine may cause one or more side effects and inclusion of the source of iodine and a reactive agent that react together to form molecular iodine with a side effect profile that is acceptable from a regulatory perspective for such ingredients will be deemed to be "pharmaceutically acceptable" levels of those ingredients.

The terms "effective amount" or "pharmaceutically effective amount" or "therapeutically effective amount" of a composition or solid dosage form as provided herein, refers to a non-toxic but sufficient amount of the composition or dosage form or ingredient therein to provide the desired response, such as preventing, diminishing, or eliminating one or more symptoms of fibrocystic breast condition in a subject. The exact amount required will vary from subject to subject, depending on the species, age, and general condition of the subject, the severity of the condition being treated (e.g., fibrocystic breast condition), the particulars of the dosage form employed, and the like. An appropriate "effective" amount in any individual case may be determined by one of ordinary skill in the art using routine experimentation.

"Treatment" or "treating" as used herein refers to controlling, preventing or otherwise reducing the occurrence, severity, or relapse of an identified symptom, condition or disease in individuals afflicted with or prone to develop such symptoms, condition or disease.

The term "patient," refers to a living organism suffering from or prone to a condition that can be prevented or treated by administration of a solid oral dosage form as provided herein, and includes both humans and animals.

"Optional" or "optionally" means that the subsequently described circumstance may or may not occur, so that the description includes instances where the circumstance occurs and instances where it does not.

"Normal storage conditions" in reference to the compositions herein is a dark environment with a temperature of 5-40° C., 10-90% humidity, 1 atm pressure, and approximately 20% oxygen and 80% nitrogen.

An ingredient in a solid dosage form is described as "unreactive" if the ingredient undergoes less than 10% change over 6 months under storage conditions at room temperature (25° C.), atmospheric pressure, and 50% humidity in air. An ingredient is said to have undergone a change if, for example, it forms a reaction product with another ingredient, forms an epimer of the molecule, or the molecule is degraded through exposure to light, moisture or oxygen.

"Cmax" refers to the peak concentration of a material after administration of a single dose of the material. Cmax is typically measured in urine or blood plasma. For iodine concentration, Cmax is measured as the concentration of total iodine in the urine.

"Tmax" refers to the time it takes for a material to reach Cmax following administration of a single dose of the material.

The "pH" or "effective pH" of a solid dosage form or dried granulation is measured by preparing a 10% (w/v) solution of the solid form or granulation in distilled water and determining the pH.

The term "pH control agent" refers to chemical(s) that control the effective pH of a dried granulation for a solid dosage form. Suitable pH control agents include sodium carbonate, calcium carbonate, potassium carbonate, magnesium carbonate, sodium hydroxide, bentonite, dibasic calcium phosphate dehydrate, magnesium oxide, magnesium trisilicate, sodium bicarbonate, dibasic sodium phosphate, and tribasic potassium phosphate.

A mixture that is referred to, interchangeably, as "homogeneous" or as having a "homogeneous distribution" is a mixture in which the concentration for each of the sampled ingredients typically has a relative standard deviation of less than 5% when 10 or more samples of 0.1 to 10 mg are taken from different locations within the mixture where a source of iodine is present. For a solid dosage form, the homogeneous distribution is usually assessed for the dried granulation matrix that contains the active ingredients prior to compression forming a solid form. If a solid oral dosage form includes multiple granulation mixtures, such as a granulation mixture with an enteric coating and a granulation mixture without an enteric coating, whether the solid oral dosage form is homogenous will be determined based on the homogenous distribution of each granulation mixture separately. It is not required that the two mixtures be evenly distributed within a solid oral dosage form for it to be considered a homogenous distribution of selected ingredients. If a solid oral dosage form includes multiple portions, such as a portion with an enteric coating and a portion without an enteric coating, then the source of iodine and the reactive agent are said to be mixed in a homogenous distribution if they are mixed in a homogenous distribution within either portion of the solid oral distribution.

The terms oxidant, oxidizer, and oxidizing agent are used interchangeably to refer to an element or compound that accepts one or more electrons in an oxidation-reduction reaction with at least one other chemical.

The terms reductant, reducer, and reducing agent are used interchangeably to refer to an element or compound that donates one or more electrons in an oxidation-reduction reaction with at least one other chemical.

Overview

An ideal drug produces its desired effect in all patients without causing adverse toxic effects. The relationship between the desired and undesired effects of a drug is termed its therapeutic index or selectivity. The therapeutic index for a drug is frequently represented as the ratio of the median toxic dose to the median effective dose. In clinical studies, drug selectivity is often expressed indirectly by summarizing the pattern and nature of adverse effects produced by therapeutic doses of the drug and by indicating the proportion of patients with adverse side effects. One goal of the solid oral dosage forms and methods provided herein is to increase the therapeutic index of a solid oral dosage form that generates molecular iodine in the stomach.

Molecular iodine has been used to treat a number of disease states and conditions. U.S. Pat. Nos. 4,816,255; 5,171,582; 5,250,304; 5,389,385; and 5,589,198, describe compositions of molecular iodine ($I_2$) in water, or in a carrier, for oral administration to patients who are iodine deficient to treat a variety of human diseases and conditions, including fibrocystic breast condition.

The use of a stable solid oral dosage form that creates molecular iodine in the stomach reduces the risk of thyroid related adverse events such as hypo- and hyper-thyroidism when compared to dosage forms comprising iodide salts. However, since women greater than 40 years of age experience thyroid-related adverse events at a rate estimated to be six-fold higher than men, it is important to increase the safety of any such solid oral dosage form that will be used in this population. Therefore, when considering chronic dosing of iodine in amounts in excess of 1.1 mg per day, it is important to develop an iodine-based formulation that protects the thyroid gland to the greatest degree possible.

Thyroid weight is one diagnostic metric used to evaluate thyroid status and which therefore can be used to evaluate the toxicity of an iodine solid oral dosage form in mammals. As an illustration, subchronic administration of iodide to male rats increased the weight of the thyroid gland of the rats at an iodide concentration of 10 mg per kg of body weight; molecular iodine did not significantly affect thyroid weight even at concentrations of 100 mg per kg of body weight (Sherer et al., *Journal of Toxicology and Environmental Health*, Vol. 32, pp. 89-101, 1991, "Comparison of Toxicity Induced by Iodine and Iodide in Male and Female Rats"). In another study in mice, Thrall et al. found that "Since thyroid uptake of iodine is specific for I⁻ [iodide], this suggests that the form of iodine in the blood was different in animals administered $I_2$ [molecular iodine]. This notion was further supported by the finding that pretreatment of animals with varying concentrations of I⁻ in drinking water was four times as effective in suppressing the uptake of a test dose of $^{125}I^-$ than pretreatment with equivalent concentrations of $I_2$." (K D Thrall and R J Bull, *Fundamental and Applied Toxicology* 15, 75-81 (1990), "Differences in the Distribution of Iodine and Iodide in the Sprague-Dawley Rat") The Sherer and Thrall studies demonstrate that iodide affects thyroid weight in mammals at concentrations that are significantly less than a comparable effect from molecular iodine. In other words, these findings suggest that it requires several times more molecular iodine than iodide to affect animal thyroid function.

Chronic daily iodine administration has been demonstrated in controlled clinical trials to provide a clinical benefit to some patients for symptoms not associated with thyroid hormones. For example, it has been reported that for an equal dose of total iodine, less iodine partitions into the thryoid when administered orally as molecular iodine than if administered orally as iodide (K D Thrall and R J Bull, *Fundamental and Applied Toxicology* 15, 75-81 (1990), "Differences in the Distribution of Iodine and Iodide in the Sprague-Dawley Rat"). For this reason, molecular iodine appears to be less thyrotoxic than iodide. Provided herein is a solid oral dosage form that minimizes the potential for thyroid related adverse events during chronic (e.g., daily) administration of molecular iodine at quantities ranging from 3 to 60 mg per unit dose. Moreover, it has been discovered that higher than previously considered attainable therapeutically effective doses of total iodine as provided in the compositions herein, comprising a source of molecular iodine, where the molecular iodine is generated in vivo upon exposure to the gastric environment, are deliverable to a subject, in safe dosage amounts up to 60 milligrams per day. See, e.g., Example 7.

The solid oral dosage form provided herein is effective to treat fibrocystic breast condition and/or the symptoms associated with fibrocystic breast condition, such as cyclical breast pain, breast tenderness, and breast nodularity. The solid oral dosage form comprises a source of iodine, a reactive agent capable of reaction with the source of iodine, and calcium or iron. The source of iodine is unreactive when the solid oral dosage form is maintained under normal storage conditions. When the solid oral dosage form is exposed to gastric conditions such as those found in the stomach, or in simulated gastric fluid (SGF), the source of iodine reacts with the reactive agent to generate molecular iodine in a ratio of molecular iodine to total iodine in the range of 0.8 to 1.0 by weight. The total iodine content comprised in the solid oral dosage form provided herein may be, for example, in a range of from 3 to 60 mg, resulting in a quantity of molecular iodine in SGF of 2.4 to 60 mg. For example, for a solid dosage form as provided herein having a total iodine content of from greater than 6 to 50 mg, the resulting quantity of molecular iodine generated in SGF would be from greater than 4.8 to 50 mg.

The solid oral dosage form is typically delivered daily to treat symptoms related to fibrocystic breast condition and to prophylactically maintain breast health in pre-menopausal women. One key symptom of fibrocystic breast condition is monthly cyclical breast pain that typically occurs just before or during the initial phases of a woman's period (i.e., just before or during menses). Breast pain associated with fibrocystic breast condition can be minimized or reduced upon formation of iodinated lipids in vivo. Iodinated lipids are formed by a reaction of lipophilic molecular iodine with lipids within the body. The resulting iodinated lipids have an antiproliferative effect that limits hyperplasia and dysplasia of breast tissue. Iodinated lipids induce an apoptotic effect in certain breast cells, such as pre-cancerous cells and cancer cells. By inducing apoptosis in breast cells, iodinated lipids reduce the swelling and excess tissue that can cause breast pressure and breast pain.

When consuming supraphysiological doses of iodine, the amount of iodine that is taken up by the thyroid should be minimized, particularly with long-term usage. As described supra (Thrall and Bull), to achieve similar thyroid effects in equivalent populations, the molecular iodine concentration would be approximately 4 times the iodide concentration. Therefore, to minimize the impact on the thyroid, molecular iodine is the preferred form for incorporation in the dosage forms described herein. Thus, it is important to generate a high ratio of molecular iodine to iodide in order to minimize the impact on the thyroid. Preferably, the ratio of molecular iodine to total iodine (by weight) upon exposure of the solid oral dosage form to simulated gastric fluid is at least 0.80. More preferably, the ratio is at least 0.90 or at least 0.95.

Although therapeutically desirable, there exists a technical challenge in ensuring a high ratio of molecular iodine to total iodine in a therapeutic solid oral dosage form. Molecular iodine is generated, for example, by oxidation of iodide by iodate. However, this is not the only reaction path for iodide. Iodide reacts with either (1) molecular iodine to form triiodide or (2) iodate to form molecular iodine. Several formulation factors contribute to a solid oral dosage form that achieves a high ratio of molecular iodine to total iodine.

First, a source of iodine along with a suitable reactive agent are selected, such the both are stable when in formulation and react to form molecular iodine when exposed to SGF or stomach acid for a period of up to 2 hours, or preferably for a period of 1 to 60 minutes, or more preferably for a period of 60 minutes. The reaction between the source of iodine and the reactive agent can be, for example, an oxidation-reduction reaction that occurs in SGF, such as would happen between potassium iodide and potassium iodate. Additional examples are given in the section infra entitled, "Iodine."

Second, maintaining the stability of the ingredients in the solid oral dosage assists in achieving a high ratio of molecular iodine to total iodine throughout the shelf life of the solid oral dosage form. To enhance stability of some ingredients, such as iodate salts and iodide salts, a pH control agent can be used to increase the effective pH of the solid oral dosage form to between 7.0 and 12.0, to between 8.0 and 12.0, or to between 9.0 and 12.0. Since the solid oral dosage form is designed for reaction of the source of iodine with the reactive agent in the low pH environment of SGF, preferred embodiments maintain the pH of the solid dosage form between 7.0 and 12.0, between 8.0 and 12.0, or between 9.0 and 12.0. If the solid oral dosage form does not contain the source of iodine and the reactive agent distributed throughout, then, in some embodiments, only the portion containing these two ingredients contains the pH control agent.

Third, a high ratio of molecular iodine to total iodine is created by developing a solid oral dosage form in which the source of iodine reacts with the reactive agent and not with molecular iodine as it is generated. This end is achieved, for example, by ensuring a molar ratio between iodide and iodate of about 5:1. In another example, an iodide salt (e.g., potassium iodide, sodium iodide, or rubidium iodide) is combined with and reacts with a ferric salt (e.g. ferric oxide) in a molar ratio of about 4:1. In another example, an iodide salt is combined with and reacts with manganese dioxide (i.e., manganese (IV) oxide) in a molar ratio of about 2:1. In preferred embodiments, the ratio of the source of iodine to the reactive agent is within ±20% of a ratio that creates a ratio of molecular iodine to total iodine within the range 0.97 to 1.0. For example, in a solid oral dosage form comprising an iodide salt and an iodate salt, the ideal ratio of iodide ($I^-$) to iodate ($IO_3^-$) is 5:1 and ±20% of this idealized ratio corresponds to a range of 4:1 to 6:1.

Fourth, a high ratio of molecular iodine to total iodine is created for a solid oral dosage form by ensuring a homogenous distribution of the source of iodine and the reactive agent. If the solid oral dosage form does not contain the source of iodine and the reactive agent distributed throughout, then the ratio of molecular iodine to total iodine is only affected by the portion containing either of these ingredients and the homogenous distribution could be limited to that portion of the solid oral dosage form. In some embodiments, the iodide and iodate salt(s) are first dissolved in a suitable solvent to allow their homogenous distribution throughout the solid dosage form. This allows the ratio between the iodide and iodate salts to fall within a desired ratio throughout the tablet.

Administration of molecular iodine alone is not sufficient for all patients suffering from fibrocystic breast condition. For those at an increased rate of risk of thyroid related adverse events due to, e.g., nutritional deficiencies in one or more of the minerals iron, calcium, and selenium, systemic exposure to chronic supraphysiological levels of iodine, even in the form of molecular iodine, can have negative effects on the thyroid. Intra-thyroidal and extra-thyroidal cofactors, enzymes, proteins and hormones influence thyroid hormone synthesis and regulation. An increase in the incidence of adverse thyroid related clinical outcomes may arise if there is a deficiency in one or more of these elements. The solid oral dosage form provided herein reduces the risk to the thyroid from adverse clinical outcomes during chronic dosing of supraphysiological levels of molecular iodine by addressing such potential deficiencies. In addition, the solid oral dosage form described herein is effective to reduce the risk of side effects caused by an imbalance of thyroid hormones and/or by factors that can lead to such an imbalance. This is important because the risk of thyroid related adverse events is increased under chronic daily dosing at supraphysiological levels. In particular, the solid oral dosage form addresses potential thyroid-related adverse events for those patients who have deficiencies in iron, calcium, and/or selenium that may interfere with the thyroid.

Increased safety is accomplished by providing a defined concentration of one or more of the following three cofactors: selenium, calcium, and iron. These cofactors are required for enzymes or transport processes involved in thyroid hormone synthesis and regulation. In addition, two vitamins, A and D, which enhance absorption of the cofactors, are preferentially incorporated into the solid oral dosage forms described herein. Finally, additional ingredients are preferably incorporated into the instant solid oral dosage forms to increase the effectiveness of treatment of cyclic breast pain by reducing the baseline level of breast pain by administration of the solid oral dosage forms provided herein for patients with fibrocystic breast condition. Various combinations of co-factors can be included depending on the needs of the subject or population; the solid oral dosage form may, for example, comprise (1) selenium and calcium, (2) selenium and iron, or (3) selenium, calcium, iron, vitamin A, and vitamin D.

In some embodiments, the solid dosage form comprises, in addition to the source of molecular iodine, calcium and vitamin A. In some embodiments, the solid dosage form comprises, in addition to the source of molecular iodine, iron and vitamin D. In embodiments in which vitamins A and/or D or comprised within the dosage form, the vitamins may comprise an enteric coating. Such enteric coating is effective to limit the interaction between the vitamin A and/or D and the molecular iodine that is generated in the stomach. As shown in Examples 2-4, even under conditions such as those in the stomach, molecular iodine was found to bind with vitamin A and vitamin D. The iodination of the vitamins within the environment of the stomach thereby reduced the effective amount of molecular iodine available for treatment. Moreover, the beneficial therapeutic effect of the vitamins may be similarly hampered by their complexation with the molecular iodine generated. Thus, the use of an enteric coating or other similar mechanism of physical separation or encapsulation of the vitamins is effective to prevent or reduce their reaction with the molecular iodine that is generated in vivo.

In some embodiments, the solid dosage form comprises, in addition to the source of molecular iodine, calcium and/or iron, one or more ingredients selected from the group consisting of GLA, vitamin B1, magnesium, and zinc. Such ingredients may be useful for reducing the baseline level of discomfort experienced by patients to thereby enhance the overall effectiveness of the molecular iodine in the treatment of symptoms of fibrocystic breast condition.

Additional examples of embodiments of the solid oral dosage form comprising the three co-factors (iron, calcium, and selenium) and additional ingredients that may enhance the effectiveness of the dosage form are provided in the following sections along with details on the appropriate levels for inclusion in the solid oral dosage form and methods for fabricating the solid oral dosage form.

Iodine

Molecular iodine itself is generally not stable when comprised in solid oral dosage forms under normal storage conditions. Therefore, it is preferable to incorporate into the instant formulations ingredients that generate molecular iodine in the stomach or in simulated conditions thereof, such as in SGF (simulated gastric fluid), due both to the reduced toxicity of molecular iodine in comparison to iodide, and the ability to safely administer to a subject much higher levels of molecular iodine than have been previously considered to be both acceptable and safe. See, e.g., Example 7. This can be accomplished by combining a source of iodine with a reactive agent, where the desired ultimate application is an in vivo reaction in the stomach. SGF is used as a model system to indicate whether the source of iodine/reactive agent will generate molecular iodine in the acidic environment of the stomach. Exemplary combinations that can be used to generate molecular iodine in SGF include (1) oxidants comprising iodine (iodine oxidizer) combined with reductants comprising iodine (iodine reducer), (2) sources of ferric iron (e.g., ferric salts) plus sources of iodide (e.g., iodide salts), (3) sources of iodide plus oxidants, and (4) sources of iodate plus reductants. Preferably, ingredients of the solid oral dosage form generate molecular iodine when mixed with SGF (and in stomach acid) and are present in the solid dosage form to provide a total iodine content therein of from 3 to 60 mg (e.g., 3, 5, 10, 20, or 60 mg), 6 to 50 mg (e.g., 6, 15, 20, or 50 mg), or 9 to 40 mg (e.g., 9, 16, 32, or 40 mg). The total iodine content in the solid dosage form may be, for example, from greater than 6 milligrams to 60 milligrams, from greater than 6 milligrams to 50 milligrams, from greater than 6 milligrams to 40 milligrams, from 7 milligrams to 50 milligrams, from 8 milligrams to 40 milligrams, from 9 milligrams to 30 milligrams, from 9 milligrams to 25 milligrams, or from 10 milligrams to 25 milligrams.

As demonstrated through the studies described infra in Examples 1, 6, and 7, these dosage levels are safe for use in humans. The solid oral dosage form, when placed in simulated gastric fluid, generates a ratio of molecular iodine to total iodine in the range of 0.8 to 1.0 by weight. As demonstrated in Example 5, it is preferred that the distribution of the source of iodine and the reactive agent be homogenous.

Examples of combinations falling within category 1 above are described in U.S. Pat. Nos. 5,885,592 and 6,248,335, which are herein incorporated by reference. For this category, the ratio of the iodine oxidizer to iodine reducer is selected so that the predominant species of iodine in the stomach (as simulated by SGF) is molecular iodine. For salts of iodide and iodate, the preferred molar ratio between the iodide and iodate is 5:1. For combinations in category 1, either iodide or iodate may serve the role of the source of iodine while the other serves the role of the reactive agent to thereby generate molecular iodine.

For many of the ferric salts described in category 2, the iron is converted from ferric to ferrous iron following the oxidation of iodide to molecular iodine. Examples in category 2 include combinations of ferric oxide and potassium iodide and/or sodium iodide. When these are immersed in a low pH environment, such as stomach acid or SGF, they undergo the following reaction: $Fe_2O_3 + 6\ H^+ + 4\ KI \rightarrow 2\ FeK_2 + 2\ I_2 + 3\ H_2O$ and/or $Fe_2O_3 + 6\ H^+ + 4\ NaI \rightarrow 2\ FeNa_2 + 2\ I_2 + 3\ H_2O$. In this example, the preferred molar ratio between the source of iodine (i.e., potassium iodide or sodium iodide) and the reactive agent (i.e., ferric oxide) is 4:1.

Examples in category 3 include manganese dioxide plus potassium iodide and/or sodium iodide. When these are immersed in a low pH environment, such as stomach acid or SGF, they undergo the following reaction: $MnO_2 + 4H^+ + 2KI \rightarrow K_2Mn + I_2 + 2\ H_2O$ or $MnO_2 + 4H^+ + 2NaI \rightarrow Na_2Mn + I_2 + 2\ H_2O$. In this example, the preferred molar ratio between the source of iodine (i.e., potassium iodide or sodium iodide) and the reactive agent (i.e., manganese dioxide) is 2:1. Another suitable combination is an iodide salt plus a nitrate salt. When these are immersed in a low pH environment, such as stomach acid or SGF, they undergo the following reaction: $NO_3^- + 4H^+ + 2I^- \rightarrow NO + I_2 + 2H_2O$, via an intermediate reaction that produces $HNO_2$ and $H_2O$. In this example, the preferred molar ratio between the source of iodine (i.e., an iodide salt) and the reactive agent (i.e., a nitrate salt) is 2:1. Another suitable example in this category is an iodide salt plus a source of hydrogen peroxide or an organic hydroperoxide, in combination with a peroxidase as a catalyst. Examples of peroxidases include horseradish peroxidase, soybean peroxidase, lactoperoxidase, myerloperoxidase, NADH peroxidase, NDAPH peroxidase, fatty-acid peroxidase, cytochromes-c peroxidase, catalase, glutathione peroxidase, L-ascorbate peroxidase, phospholipid-hydroperoxide glutathione peroxidase, manganese peroxidase, lignin peroxidase, peroxiredoxin, versatile peroxidase, glutathione amide-dependent peroxidase, bromide peroxidase, dye decolorizing peroxidase, prostamide/prostaglandine F2α synthase, catalase-peroxidase, and hydroperoxy fatty acid reductase.

Depending on the selected embodiments and the amount of deviation from the ideal molar ratios described above, the solid oral dosage form, when placed in SGF, is effective to generate a ratio of molecular iodine to total iodine in the range of 0.8 to 1.0 by weight (e.g., 0.8, 0.85, 0.9, 0.95, or 1.0), preferably 0.9 to 1.0 (e.g., 0.9, 0.95, or 1.0), more preferably 0.95 to 1.0 (e.g., 0.95, 0.97, 0.98, or 1.0), or yet more preferably 0.97 to 1.0 (e.g., 0.97, 0.98, 0.99, or 1.0).

In addition to iodine, the solid oral dosage form contains one or more of the following components: calcium, iron, selenium, vitamin A, and vitamin D.

Calcium

On the luminal side of the apical membrane of the follicular lumen of the thyroid, iodide is oxidized by thyroid peroxidase (TPO), a reaction that requires the presence of hydrogen peroxide ($H_2O_2$). Peroxide is generated by the calcium-dependent flavoprotein nicotinamide adenine dinucleotide phosphate (NADPH) oxidase dual oxidase 2 (DUOX2), an enzyme that requires an additional protein named dual oxidase maturation factor 2 (DUOXA2). The DUOX gene encodes these two proteins that have an 83% homology and are closely related to gp91Phox and a superoxide generating oxidase (MOX1) all of which include a "finger" binding domain that contains calcium binding sites necessary for peroxide generation from cytosolic calcium. In addition, DUOX2 requires micromolar concentrations of calcium for activity. Without sufficient calcium, iodide is not adequately oxidized in the thyroid, potentially leading to an underproduction of thyroid hormones (T3 and T4) and iodinated lipids. Providing adequate calcium is particularly important when chronically dosing with supraphysiological levels of iodine due to adjustments in thyroid regulation under such conditions. The optimal level of calcium can be further refined through experiments as shown in Example 8. The results in Example 8 further demonstrate the synergistic effects of certain metals (i.e., Ca, Fe, Se) in returning to/achieving normal thyroid function in a subject post-administration of iodine. Administration of a composition as provided herein comprising, in addition to a source of molecular iodine and at least one of calcium or iron, at least two of the foregoing three metals to thereby achieve the associated benefits with respect to maintaining normal thyroid function. For example, the solid dosage form may comprise as metal ions, a combination of calcium and iron, a combination of calcium and selenium, a combination of iron and selenium, and a combination of all three at their respective preferred dosage amounts as provided herein. Thus, administration of a formulation as provided herein comprising a combination of at least two of the metals illustrated to have a synergistic effect at the dosage levels described herein, is effective to provide a faster return to normal thyroid function or maintenance of thyroid function when compared to the same composition absent the synergistic combination, as determined by measurement of any one of thyroid hormones TSH, T3 or T4. Preferably, measurements are based upon a comparison of TSH levels.

Calcium for use in the solid dosage form can be provided in many forms. Examples of sources of calcium include calcium carbonate, calcium citrate, amino acid chelate, citrate-malate, calcium gluconate, tricalcium phosphate, or various forms of algae (e.g., Lithothamnion: *L. calcareum* and *L. corallioides*). The amount of calcium included in the solid dosage form is preferably 10 to 500 mg (e.g., 10, 50, 100, 300, or 500 mg), more preferably 10 to 200 mg (e.g., 10, 40, 120, or 200 mg), and most preferably 20 to 100 mg (e.g., 20, 40, 70, or 100 mg).

Iron

Peroxidases are enzymes that reduce hydrogen peroxide to water. TPO, like all peroxidases, contains a prosthetic heme group that helps shuttle reducing equivalents to convert hydrogen peroxide to water and concomitantly (a) oxidize iodide to molecular iodine and (b) oxidize iodinated tyrosyl moieties to free radicals. Both molecular iodine and tyrosyl free radicals are required for iodination of thyroglobulin (Tg) and cross-linking of iodinated Tg-tyrosyl groups in the follicular lumen to form nascent T4 and T3.

The absence of the heme porphyrin totally eliminates all TPO oxidase activity. Consequently, it is important to ensure that patients receiving iodine solid oral dosage forms have sufficient iron since a reduced ability to oxidize iodide means that the hydrogen peroxide generated by the thyroid gland will detrimentally oxidize a higher proportion of adjacent thyroid tissue. Clinical studies have been made on goitrous iodine-deficient children who were either iron sufficient or iron-deficient (anemic) (Zimmerman M, et al. European Journal of Endocrinology (2000) 142; 217-223). Both groups were given oral doses of iodized oil. Thyroid gland volume was measured using ultrasound to define goiter post intervention. The prevalence of goiter at 30 weeks after oral iodized oil administration in the iron-sufficient group was 12% and the prevalence in the iron-deficient (anemic) group was 64%. After iron supplementation in the anemic group, the goiter prevalence fell to 31% and 20% at 50 and 65 weeks, respectively. The optimal level of iron can be further refined through experiments as shown in Example 8.

The target range for the amount of iron included in the solid dosage form is preferably 0.2 to 20 mg (e.g., 0.2, 1, 3, 5, 7, 10, 15, or 20 mg). More specific target ranges for iron depend on the availability of iron in the diet of the target population. For example, populations with a high rate of iron deficiency in the diet and those unlikely to have additional iron supplementation benefit from a higher dose of iron, such as 5 to 20 mg (e.g., 5, 8, 12, 15, or 20 mg). Populations with a low rate of iron deficiency in the diet benefit from a lower dose of iron, such as 0.2 to 5 mg (e.g., 0.2, 1, 2, 3, or 5 mg), to reduce the incidence of iron overload.

Iron for use in the solid dosage form can be provided in many forms. Examples of sources of iron include ferric citrate, ferrous sulfate, iron amino acid chelate, ferrous fumarate, ferrous succinate, ferric pyrophosphate, iron gluconate, carbonyl iron, and iron bisglycinate.

Selenium

Deiodinases play a critical role in regulating thyroid hormone activity during development of the neonate and selenium deficiency can lead to imbalances in thyroid hormone activity in adults. Selenium is an essential co-factor for all three types of deiodinases (D1, D2 and D3) found in humans. For instance, selenium-deficient humans are known to exhibit increased ratios of T4 to T3.

D2 is a seleno-deiodinase that catalyzes the conversion of T4 to T3 in many tissues, including bone, skin, and skeletal muscle. D2 activity creates a substantial fraction of the tissue specific T3 generated outside the thyroid which is critical to maintain the desired ratio between the concentrations of T3 and T4 in the blood and extra-thyroidal body tissues.

D3 catalyzes the conversion of T4 and T3 to biologically inactive iodinated thyronines, specifically, reverse T3 and 3,3'-diiodothyronine. Thus, D3 contributes to thyroid hormone homeostasis by protecting tissues from an excess of thyroid hormone. In humans, D3 is present in the skin, central nervous system (CNS), and placenta. D3 is critical for thyroid hormone homeostasis, because it protects the fetus from premature exposure to excess amounts of thyroid hormone, which can result in malformations, altered growth, mental retardation, and even death. In fetal and neonatal animals, D3 expression is highly regulated in tissue-specific patterns that are likely to be critical to the coordinated regulation of thyroid hormone for normal development.

Selenium for use in the solid dosage form can be provided in many forms. Examples of sources of selenium include selenium yeast, L-selenomethionine, methylselenocysteine, sodium selenate, and sodium selenite. The optimal level of selenium can be further refined through experiments as shown in Example 8. The amount of selenium included in the solid dosage form, if present, is preferably 25 to 100 µg (e.g., 25, 30, 50, 70, or 100 µg), more preferably 40 to 100 µg (e.g., 40, 45, 70, or 100 µg), and most preferably 70 to 90 µg (e.g., 70, 75, 85, or 90 µg).

Vitamins A and D

Thyroid hormone action is mediated by nuclear receptors with high affinity for thyroid hormones. Thyroid hormones exert their nuclear actions through thyroid hormone receptors (TRs) alpha and beta, which bind to deoxyribonucleic acid (DNA) regulatory elements in thyroid hormone-responsive genes.

TRs are members of the nuclear hormone receptor superfamily, each of which includes vitamin A and D receptors. T3 is either transported into the cell or formed intracellularly from T4 by deiodinase D2. T3 then enters the nucleus, where it binds to the nuclear TRs with high affinity and specificity. TR is a ligand-regulated transcription factor that is intimately associated with chromatin and heterodimerizes with another member of the nuclear receptor superfamily, retinoid X receptor (RXR). The TR/RXR complex can then bind to target DNA sequences known as TH-response elements located in the promoter regions of target genes. The RXR proteins are the most important binding partners for thyroid hormones. RXR heterodimerizes with the retinoic acid (a metabolite of vitamin A) and vitamin D receptors, and promotes binding to their respective hormone response elements. Thus, vitamins A and D are beneficial in promoting binding of thyroid hormones with RXR proteins. This binding enables thyroid hormones to exert their influence on cell nuclei.

In addition, both Vitamin A and D promote absorption of different nutritional co-factors that are necessary for effective thyroid metabolism. For example, vitamin A promotes absorption of iron and Vitamin D promotes absorption of calcium.

The amount of vitamin A included in the solid dosage form is preferably 10 to 1000 µg (e.g., 10, 100, 300, 500, 800, 900, or 1000 mg), more preferably 10 to 500 µg (e.g., 10, 30, 60, 200, 300, or 500 µg), and most preferably 50 to 300 µg (e.g., 50, 100, 200, or 300 µg). The amount of vitamin D included in the solid dosage form is preferably 1 to 30 µg (e.g., 1, 5, 10, 25, or 30 µg), more preferably 1 to 10 µg (e.g., 1, 3, 6, 8, or 10 µg), and most preferably 2 to 5 µg (e.g., 2, 3, 4, or 5 µg). Vitamin D is preferably provided as Vitamin D3. The optimal level of vitamins A and D can be further refined through experiments as shown in Example 8. The optimal level of vitamins A and D will vary with the amount of iron and calcium, respectively, for example, in the solid dosage form. As described above, the vitamins are preferably enterically coated.

Enteric Coating

Although in certain embodiments it is desirable to administer vitamins A and/or D in combination with ingredients that form molecular iodine in the stomach or in SGF, a direct, co-intimate mixture is undesirable in many embodiments. As shown in Examples 3 and 4, molecular iodine can iodinate both vitamins A and D if they are both present and accessible within the stomach. Iodination of vitamins A and D alters their structure and thus reduces their biologic activity, in addition to consuming molecular iodine generated by the dosage form intended for use in treating the symptoms of fibrocystic breast condition. Thus, there is a problem that needs to be overcome to deliver vitamin A and/or D in the same solid oral dosage form along with the ingredients that form molecular iodine in the stomach or in SGF. To limit the interaction between molecular iodine and vitamins A and/or D within the stomach, the molecular iodine is physically separated from the vitamins A and/or D in the solid dosage form in a manner that limits or prevents any interaction between the molecular iodine and the vitamin(s) in vivo. Ideally, the goal of the enteric coating is to allow the molecular iodine to be formed and absorbed in the stomach and the vitamins to be released in the lower GI tract where the pH environment is elevated relative to the stomach. In one or more exemplary embodiments of physical separation, an enteric coating is used to coat the vitamins A and/or D within the solid dosage form. In one or more alternative exemplary embodiments, the vitamins or the sources of molecular iodine are encapsulated within the solid dosage form, such as with liposomes, in a manner that limits their interaction. In one or more yet alternative exemplary embodiments, the vitamins or the sources effective to generate molecular iodine in vivo are incorporated into microparticles within the solid dosage form.

In preferred embodiments, an enteric coating is used to coat the vitamins A and/or D within the solid dosage form to limit interaction between the vitamins A and/or D and molecular iodine. In one or more embodiments, (1) the portions of the solid oral dosage forms that contain the ingredients required to form molecular iodine are designed to dissolve within a pre-defined timeframe in the stomach or in SGF, such as within 4 hours, and (2) these portions are coupled with an enteric coated vitamin A and/or D within the solid dosage form. Providing a portion of the solid oral dosage form that dissolves within the stomach allows molecular iodine to be formed in the stomach where it is absorbed before vitamins A and/or D are released from the enteric coating. Examples of materials that may be included in the portion that is designed to dissolve within the stomach in a pre-defined timeframe include lactose, sucrose, sorbitol, and disintegrants, such as sodium starch glycosylate. These ingredients dissolve within 4-8 hours, within 2-4 hours, within 1-2 hours, or within 2 hours for solid dosage forms of typical size for most compositions. Examples of enteric coatings will be familiar to those skilled in the art and include lipids, waxes, plastics, plant fibers, polymers (e.g., hydroxypropyl methylcellulose, methacrylic acid-ethyl acrylate copolymer, EUDRAGIT polymers (Evonik Industries AG, Essen, Germany)), and cellulose derivatives. The enteric coating is designed to deliver ingredients (e.g., vitamins) to the gastrointestinal tract below the stomach. As demonstrated in Example 1, essentially all molecular iodine administered to the stomach is absorbed from the stomach, but any molecular iodine that might pass through to the lower gastrointestinal tract would be rapidly hydrolyzed since molecular iodine is not stable above a pH of 7 (Hickey J, Panicucci R, Duan Y, Dinehart K, Murphy J, Kessler J, Gottardi W. *J Pharm Pharmacol.* 1997 December; 49(12): 1195-9).

Synergies Among Co-Factors

The co-factors described in this application (i.e., selenium, iron, and calcium) can act synergistically. Deficiencies of selenium, iron, and vitamin A in the presence of adequate calcium can predispose a patient to the development of goiter, by (i) increasing peroxides that damage the thyroid gland and impairing deiodinase activity, (ii) reducing thyroperoxidase activity, and (iii) decreasing vitamin A-mediated suppression of the pituitary TSH beta gene.

Not all co-factors are provided in solid oral dosage forms that are manufactured for all populations. Some populations have a high incidence of deficiencies in certain cofactors, while having low incidence of deficiencies in other cofactors. For example, a particular region may have a high incidence of calcium deficiency, but a low incidence of iron deficiency. In such a region, it would be appropriate to provide a solid oral dosage form that contains calcium, but does not contain iron. Even though all cofactors are beneficial, not all cofactors are necessary or advantageous for inclusion in the iodine solid oral dosage form across all populations.

Additional Effectiveness for Breast Pain

Painful stimuli are perceived by the same person differently if the person has a higher baseline pain level, such as from other painful stimulus. In many patients, breast pain will be felt more acutely when the baseline level of pain is higher. For subjects whose baseline pain level is relatively low, the pain associated with fibrocystic breast condition will be less than if the subjects have a moderately high baseline level.

Since fibrocystic breast condition pain is cyclical and occurs primarily just before or during the initial phases of a woman's period, the baseline pain level for such subjects can be reduced by the addition of one or more ingredients that have the effect of reducing cyclical pain at this time within the cycle. Such ingredients include GLA (gamma-linolenic acid, which is an omega-6 fatty acid, commonly found in evening primrose oil, black currant seed oil, and borage oil), vitamin B1, magnesium, and zinc.

The effectiveness of such additions can be demonstrated in a straightforward controlled comparative clinical study.

The amount of GLA included in the solid dosage form is preferably 30 to 300 mg (e.g., 30, 50, 100, 150, 200, or 300 mg) and more preferably 50 to 150 mg (e.g., 50, 70, 100, 120, or 150 mg). The amount of vitamin B1 included in the solid dosage form is preferably 1 to 100 mg (e.g., 1, 5, 10, 20, 40, 70, or 100 mg) and more preferably 1 to 10 mg (e.g., 1, 2, 3, 5, 8, or 10 mg). The amount of magnesium included in the solid dosage form is preferably 5 to 350 mg (e.g., 5, 10, 40, 90, 250, or 350 mg), more preferably 10 to 100 mg (e.g., 10, 20, 40, 70, or 100 mg), and most preferably 20 to 50 mg (e.g., 20, 30, 40, or 50 mg). The amount of zinc included in the solid dosage form is preferably 0.5 to 20 mg (e.g., 0.5, 3, 6, 15, or 20 mg), more preferably 1 to 10 mg (e.g., 1, 2, 5, or 10 mg), and most preferably 1 to 4 mg (e.g., 1, 2, 3, or 4 mg).

In certain embodiments, the solid dosage form is absent GLA.

The solid oral dosage form comprises, in addition to the sources for generating molecular iodine in the stomach, calcium or iron. The dosage form may further comprise one or more of selenium, vitamin A, vitamin D, or GLA in an amount or amounts as previously described herein. In some embodiments, the solid oral dosage form comprises no more than 5 minerals in total. In some additional embodiments, the dosage form comprises no more than 7 vitamins in total. In certain embodiments, the formulation is absent selenium. In certain embodiments, the formulation is absent GLA. In some additional embodiments, the formulation is absent selenium and GLA.

Treatment Methods

The solid dosage form is preferably ingested daily for a period of at least 28 days, and preferably for at least 60 days, to provide effective relief from (i.e., a reduction in) cyclical or non-cyclical breast pain or other symptoms associated with fibrocystic breast condition such as breast tenderness and nodularity. Although daily administration is preferable, the solid dosage form may be administered non-continuously, for example, every other day, every 3 days, every 4 days, and so on.

In some embodiments, it is preferable that the solid dosage form be taken on an empty stomach to maximize the uptake of molecular iodine and to maintain a consistent daily dose.

Preferably, treatment is accompanied by no significant change in any of the following thyroid tests: T3, T4, T uptake, TSH and FT3, especially at daily doses of total iodine greater than 6 mg per day, or greater than 8 mg per day, or greater than 10 mg per day. Preferably, no significant change is indicated by values of the thyroid function markers above that are with 2 standard deviation units of control values measured absent administration of molecular iodine.

Exemplary Embodiments

The solid oral dosage form can be prepared in a number of different forms, such as pills, tablets, and capsules. Without loss of generality, the embodiments described herein are preferably in the form of a tablet. Other forms will be evident to those skilled in the art.

To form a tablet, the solid oral dosage form ingredients targeted for the small intestine (e.g., GLA and vitamins A, D, and E) are mixed and granulated using dry mixing or with a spray dry method following mixture with a solvent. The resulting granules are then coated with an enteric coating (i.e., a SGF-stable or gastric-fluid-stable film former). In a separate process, the solid oral dosage form ingredients targeted for the stomach (e.g., calcium, iron, selenium, zinc, vitamin B1, iodide salt, iodate salt, and lubricants) are mixed and granulated using dry mixing or with a spray dry method following mixture with a solvent. (In some embodiments, the ingredients targeted for the stomach are dissolved in a granulation solvent to assist in their homogenous distribution throughout the solid dosage form. This enables the ratio between the iodide and iodate salts to be in a desired ratio for samples of 1 mg or more throughout the tablet.) These two granulated mixtures are then blended together. The resulting mixture can be formed into tablets using a tablet press. Coating can be accomplished by pan spray, supercell, ACCELA-COTA (Thomas Engineering, Inc.; Hoffman Estates, Ill.), or any other method familiar to those skilled in the art of tablet making.

Film formers are selected such that they are soluble in the chosen solvent and meet the desired dissolution characteristics of the environment where the film is designed to dissolve. Examples of film formers that can be used for the enterically coated ingredients, include Cellulose Acetate Phthalate (CAP), Cellulose Acetate Trimellitate (CAT), Hydroxy Propyl Methyl Cellulose Phthalate (HPMCP), EUDRAGIT L, and Eudragit S. Examples of film formers that dissolve in SGF (and in stomach acid) are Hydroxy Propyl Methyl Cellulose (HPMC), Methyl Hydroxy Ethyl Cellulose (MHEC), EUDRAGIT E, and EUDRAGIT RL and RS.

Examples of combinations that can be used to generate molecular iodine in SGF include (1) oxidants comprising iodine (iodine oxidizer) combined with reductants comprising iodine (iodine reducer), (2) sources of ferric iron (e.g., ferric salts) plus sources of iodide (e.g., iodide salts), (3) sources of iodide plus oxidants, and (4) sources of iodate plus reductants.

Iron may be included in the form of ferric citrate, ferrous sulfate, iron amino acid chelate, ferrous fumarate, ferrous succinate, ferric pyrophosphate, ferrous gluconate, and ferrous bisglycinate.

Calcium may be included in the form of calcium carbonate, calcium citrate, amino acid chelate, citrate-malate, calcium gluconate, tricalcium phosphate, or various forms of algae (e.g., Lithothamnion: *L. calcareum* and *L. corallioides*).

Selenium may be included in the form of selenium yeast, L-selenomethionine, methylselenocysteine, sodium selenate, and sodium selenite.

Specific ingredient levels for the solid oral dosage form are selected to meet the needs of the population to which it is targeted. For example, for solid oral dosage forms being distributed to patients in regions with a high incidence of anemia, iron could be added to the solid oral dosage form, whereas it may not be necessary in regions with low rates of anemia. Examples of solid oral dosage forms according to the invention are described in Table 1. This table lists only select ingredients. It does not focus on excipient ingredients such as binders, colorants, plasticizers, etc. The amounts of those inert ingredients will typically depend on specific manufacturing or marketing requirements that are well known to those skilled in the art.

Specific combinations of ingredients are described in examples F1 to F24 in Table 1.

Combinations of elements from each of examples F1 to F24 are envisioned as embodiments of the invention. Such combinations can be made by (1) selecting an iodine source and reactive agent that react to produce molecular iodine at a total iodine content within a range as described herein, (2) selecting one or two ingredients from the iron or calcium rows, with the total amount of iron from these ingredients in a range of 0.2 to 20 mg and/or the total amount of calcium from these ingredients in a range of 10 to 500 mg. Further combinations can be made by additionally (3) optionally, selecting one or more additional ingredients from one or more of the rows for selenium, vitamin A, vitamin D, GLA, vitamin B1, magnesium, and zinc. Selected ingredients (selected by either steps 1 and 2 or by steps 1, 2, and 3), can then be combined with one or more items from the group consisting of a film former, a solvent, a plasticizer, a binder, a lubricant, a colorant, an opaquant, and an extender (or from a group consisting of any subset of that group) to produce a solid dosage form in accordance with the teachings herein.

Note that the ingredient quantities listed in Table 1, combinations thereof, and other quantities described in this application refer to the quantities for each solid oral dosage form, regardless of whether a single solid oral dosage form is prepared or multiple solid oral dosage forms are prepared in a batch. If a batch of multiple solid oral dosage forms is prepared from a single mixture of ingredients, the quantity of each ingredient is scaled based on the quantity of solid oral dosage forms produced.

TABLE 1

| | \multicolumn{6}{c}{Examples of ingredients for a solid oral dosage form} |
|---|---|---|---|---|---|---|
| | Example F1 | Example F2 | Example F3 | Example F4 | Example F5 | Example F6 |
| Iodine source | 3.54 mg sodium iodide (3 mg iodine) | 59.1 mg sodium iodide (50 mg iodine) | 1.56 mg sodium iodate (1 mg iodine) | 54.5 mg potassium iodide (41.7 mg iodine) | 2.34 mg sodium iodate (1.5 mg iodine) | 47.2 mg sodium iodide (40 mg iodine) |
| Reactive agent | 1.03 mg manganese dioxide | 16.9 mg potassium iodate (10 mg iodine) | 5.91 mg sodium iodide (5 mg iodine) | 14.1 mg potassium iodate (8.33 mg iodine) | 8.86 mg sodium iodide (7.5 mg iodine) | 13.7 mg manganese dioxide |
| Iron | 1.60 mg ferrous gluconate (0.2 mg iron) | 54.4 mg ferrous sulfate (20 mg iron) | 18.3 mg ferrous bisglycinate (5 mg iron) | 160 mg ferrous gluconate (20 mg iron) | 730 μg ferrous bisglycinate (0.2 mg iron) | 13.6 mg ferrous sulfate (5 mg iron) |
| Calcium | 25.0 mg calcium carbonate (10 mg calcium) | 1.29 g tricalcium phosphate (500 mg calcium) | 25.0 mg calcium carbonate (10 mg calcium) | 829 mg calcium citrate (200 mg calcium) | 49.9 mg calcium carbonate (20 mg calcium) | 258 mg tricalcium phosphate (100 mg calcium) |
| Selenium | 54.6 μg sodium selenite (25 μg selenium) | 239 μg sodium selenate (100 μg selenium) | 95.6 μg sodium selenate (40 μg selenium) | 218 μg sodium selenite (100 μg selenium) | 167 μg sodium selenate (70 μg selenium) | 198 μg sodium selenite (90 μg selenium) |
| Vitamin A | 10 μg vitamin A | 1000 μg vitamin A | 10 μg vitamin A | 500 μg vitamin A | 50 μg vitamin A | 300 μg vitamin A |
| Vitamin D | 1 μg vitamin D3 | 30 μg vitamin D3 | 1 μg vitamin D3 | 10 μg vitamin D3 | 2 μg vitamin D3 | 5 μg vitamin D2 |
| GLA | 30 mg (in the form borage oil) | 300 mg (in the form evening primrose oil) | 50 mg (in the form black currant seed oil) | 150 mg (in the form evening primrose oil) | 50 mg (in the form black currant seed oil) | 150 mg (in the form evening primrose oil) |
| Vitamin B1 | 1 mg | 100 mg | 1 mg | 10 mg | 1 mg | 10 mg |
| Magnesium | 5 mg | 350 mg | 10 mg | 100 mg | 20 mg | 50 mg |
| Zinc | 0.5 mg | 20 mg | 1 mg | 10 mg | 1 mg | 4 mg |
| Total iodine in formulation | 3 mg | 60 mg | 6 mg | 50 mg | 9 mg | 40 mg |

| | Example F7 | Example F8 | Example F9 | Example F10 | Example F11 | Example F12 |
|---|---|---|---|---|---|---|
| Iodine source | 26.2 mg potassium iodide (20 mg iodine) | 7.80 mg sodium iodate (5 mg iodine) | 7.85 mg potassium iodide (6 mg iodine) | 2.95-59.1 mg sodium iodide (2.5-50 mg iodine) | 6.54-54.5 mg potassium iodide (5-41.7 mg iodine) | 2.34-10.4 mg sodium iodate (1.5-6.67 mg iodine) |
| Reactive agent | 6.75 mg potassium iodate (4 mg iodine) | 29.5 mg sodium iodide (25 mg iodine) | 2.06 mg manganese dioxide | 0.780-15.6 mg sodium iodate (0.5-10 mg iodine) in a molar ratio 4:1 to 6:1 for sodium iodide to sodium iodate | 1.56-13.0 mg sodium iodate (1-8.33 mg iodine) in a molar ratio 4:1 to 6:1 for potassium iodide to sodium iodate | 8.86-39.4 mg sodium iodide (7.5-33.3 mg iodine) in a molar ratio 4.5:1 to 5.5:1 for sodium iodide to sodium iodate |
| Iron | 71.9 mg ferrous gluconate (9 mg iron) | 3.65 mg ferrous bisglycinate (1 mg iron) | 49.0 mg ferrous sulfate (18 mg iron) | 1.60-160 mg ferrous gluconate (0.2-20 mg iron) | 13.6-54.4 mg ferrous sulfate (5-20 mg iron) | 0.730-18.3 mg ferrous bisglycinate (0.2-5 mg iron) |
| Calcium | 207 mg calcium citrate (50 mg calcium) | 100 mg calcium carbonate (40 mg calcium) | 258 mg tricalcium phosphate (100 mg calcium) | 25.0 mg-1.25g calcium carbonate (10-500 mg calcium) | 25.8-516 g tricalcium phosphate (10-200 mg calcium) | 49.9-250 mg calcium carbonate (20-100 mg calcium) |
| Selenium | 74.5 μg seleno-methionine (30 μg selenium) | 239 μg sodium selenate (100 μg selenium) | 120 μg sodium selenite (55 μg selenium) | 54.6-219 μg sodium selenite (25-100 μg selenium) | 95.6-239 μg sodium selenate (40-100 μg selenium) | 167-215 μg sodium selenate (70-90 μg selenium) |
| Vitamin A | 100 μg vitamin A | 200 μg vitamin A | 700 μg vitamin A | 10-1000 μg vitamin A | 10-500 μg vitamin A | 50-300 μg vitamin A |

TABLE 1-continued

Examples of ingredients for a solid oral dosage form

| | | | | | | |
|---|---|---|---|---|---|---|
| Vitamin D | 4 μg vitamin D2 | 3 μg vitamin D2 | 15 μg vitamin D3 | 1-30 μg vitamin D3 | 1-10 μg vitamin D3 | 2-5 μg vitamin D3 |
| GLA | 100 mg (in the form black currant seed oil | 70 mg (in the form black currant seed oil) | none | 30-300 mg (in the form borage oil) | 50-150 mg (in the form evening primrose oil) | 50-150 mg (in the form black currant seed oil) |
| Vitamin B1 | 5 mg | 2 mg | 1.1 mg | 1-100 mg | 1-10 mg | 1-10 mg |
| Magnesium | 30 mg | 25 mg | 320 mg | 5-350 mg | 10-100 mg | 20-50 mg |
| Zinc | 3 mg | 3 mg | 8 mg | 0.5-20 mg | 1-10 mg | 1-4 mg |
| Total iodine in formulation | 24 mg | 30 mg | 6 mg | 3-60 mg | 6-50 mg | 9-40 mg |

| | Example F13 | Example F14 | Example F15 | Example F16 | Example F17 | Example F18 |
|---|---|---|---|---|---|---|
| Iodine source | 2.95-59.1 mg sodium iodide (2.5-50 mg iodine) | 6.54-54.5 mg potassium iodide (5-41.7 mg iodine) | 2.34-10.4 mg sodium iodate (1.5-6.67 mg iodine) | 2.95-59.1 mg sodium iodide (2.5-50 mg iodine) | 6.54-54.5 mg potassium iodide (5-41.7 mg iodine) | 2.34-10.4 mg sodium iodate (1.5-6.67 mg iodine) |
| Reactive agent | 0.780-15.6 mg sodium iodate (0.5-10 mg iodine) in a molar ratio 4:1 to 6:1 for sodium iodide to sodium iodate | 1.56-13.0 mg sodium iodate (1-8.33 mg iodine) in a molar ratio 5:1 for potassium iodide to sodium iodate | 8.86-39.4 mg sodium iodide (7.5-33.3 mg iodine) in a molar ratio 5:1 for sodium iodide to sodium iodate | 0.780-15.6 mg sodium iodate (0.5-10 mg iodine) in a molar ratio 5:1 for sodium iodide to sodium iodate | 1.56-13.0 mg sodium iodate (1-8.33 mg iodine) in a molar ratio 5:1 for potassium iodide to sodium iodate | 8.86-39.4 mg sodium iodide (7.5-33.3 mg iodine) in a molar ratio 5:1 for sodium iodide to sodium iodate |
| Iron | 1.60-160 mg ferrous gluconate (0.2-20 mg iron) | none | 0.730-18.3 mg ferrous bisglycinate (0.2-5 mg iron) | None | 1.60-160 mg ferrous gluconate (0.2-20 mg iron) | 0.730-18.3 mg ferrous bisglycinate (0.2-5 mg iron) |
| Calcium | none | 25.0 mg-1.25 g calcium carbonate (10-500 mg calcium) | none | 25.8-516 g tricalcium phosphate (10-200 mg calcium) | none | 49.9-250 mg calcium carbonate (20-100 mg calcium) |
| Selenium | none | none | 167-215 μg sodium selenate (70-90 μg selenium) | 54.6-219 μg sodium selenite (25-100 μg selenium) | 167-215 μg sodium selenate (70-90 μg selenium) | none |
| Vitamin A | 10-1000 μg vitamin A | none | 50-300 μg vitamin A | None | none | none |
| Vitamin D | none | 1-30 μg vitamin D3 | none | None | none | none |
| GLA | 30-300 mg (in the form borage oil) | 50-150 mg (in the form evening primrose oil) | none | None | none | 30-300 mg (in the form black currant seed oil) |
| Vitamin B1 | 1-100 mg | none | 1-10 mg | None | 1-10 mg | 1-10 mg |
| Magnesium | 5-350 mg | 10-100 mg | none | 5-350 mg | 20-50 mg | none |
| Zinc | 0.5-20 mg | none | 1-4 mg | 0.5-20 mg | none | 1-4 mg |
| Total iodine in formulation | 3-60 mg | 6-50 mg | 9-40 mg | 3-60 mg | 6-50 mg | 9-40 mg |

| | Example F19 | Example F20 | Example F21 | Example F22 | Example F23 | Example F24 |
|---|---|---|---|---|---|---|
| Iodine source | 2.95-59.1 mg sodium iodide (2.5-50 mg iodine) | 6.54-54.5 mg potassium iodide (5-41.7 mg iodine) | 2.34-10.4 mg sodium iodate (1.5-6.67 mg iodine) | 2.95-59.1 mg sodium iodide (2.5-50 mg iodine) | 6.54-54.5 mg potassium iodide (5-41.7 mg iodine) | 2.34-10.4 mg sodium iodate (1.5-6.67 mg iodine) |
| Reactive agent | 0.780-15.6 mg sodium iodate (0.5-10 mg iodine) in a molar ratio 4:1 to 6:1 for sodium iodide to sodium iodate | 1.56-13.0 mg sodium iodate (1-8.33 mg iodine) in a molar ratio 5:1 for potassium iodide to sodium iodate | 8.86-39.4 mg sodium iodide (7.5-33.3 mg iodine) in a molar ratio 5:1 for sodium iodide to sodium iodate | 0.780-15.6 mg sodium iodate (0.5-10 mg iodine) in a molar ratio 5:1 for sodium iodide to sodium iodate | 1.56-13.0 mg sodium iodate (1-8.33 mg iodine) in a molar ratio 5:1 for potassium iodide to sodium iodate | 8.86-39.4 mg sodium iodide (7.5-33.3 mg iodine) in a molar ratio 5:1 for sodium iodide to sodium iodate |
| Iron | 1.60-160 mg ferrous gluconate (0.2-20 mg iron) | none | 0.730-18.3 mg ferrous bisglycinate (0.2-5 mg iron) | None | 1.60-160 mg ferrous gluconate (0.2-20 mg iron) | 0.730-18.3 mg ferrous bisglycinate (0.2-5 mg iron) |

TABLE 1-continued

Examples of ingredients for a solid oral dosage form

| | | | | | | |
|---|---|---|---|---|---|---|
| Calcium | none | 25.0 mg-1.25 g calcium carbonate (10-500 mg calcium) | none | 25.8-516 g tricalcium phosphate (10-200 mg calcium) | none | 49.9-250 mg calcium carbonate (20-100 mg calcium) |
| Selenium | none | none | 167-215 µg sodium selenate (70-90 µg selenium) | 54.6-219 µg sodium selenite (25-100 µg selenium) | 167-215 µg sodium selenate (70-90 µg selenium) | none |
| Vitamin A | 10-1000 µg vitamin A | none | 50-300 µg vitamin A | None | none | none |
| Vitamin D | none | none | none | 1-30 µg vitamin D3 | none | none |
| GLA | 30-300 mg (in the form evening primrose oil) | 30-300 mg (in the form black currant seed oil) | none | None | none | none |
| Vitamin B1 | none | none | none | None | 1-100 mg | 1-100 mg |
| Magnesium | none | 5-350 mg | none | 5-350 mg | none | none |
| Zinc | none | none | 0.5-20 mg | None | 0.5-20 mg | none |
| Total iodine in formulation | 3-60 mg | 6-50 mg | 9-40 mg | 3-60 mg | 6-50 mg | 9-40 mg |

As used herein the term "excipient" refers to a pharmaceutically acceptable ingredient that is commonly used in the pharmaceutical technology for preparing solid oral dosage forms. Examples of categories of excipients include, but are not limited to, binders, disintegrants, lubricants, glidants, stabilizers, fillers and diluents. One of ordinary skill in the art may select one or more of the aforementioned excipients with respect to the particular desired properties of the solid oral dosage form by routine experimentation and without any undue burden. The amount of each excipient used may vary within ranges conventional in the art. The following references which are all hereby incorporated by reference disclose techniques and excipients used to formulate solid oral dosage forms. See The Handbook of Pharmaceutical Excipients, 4th edition, Rowe et al., Eds., American Pharmaceuticals Association (2003); and Remington: The Science and Practice of Pharmacy, 20th edition, Gennaro, Ed., Lippincott Williams & Wilkins (2000).

Exemplary embodiments of the solid oral dosage form may further comprise one or more of the following excipient ingredients: solid carriers or diluents (e.g. a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc), binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), adjuvants, fillers, antioxidants, glidants, flavor enhancers, colorants, opaquants, and extenders. Each of the above excipients represents a separate embodiment of the present invention.

In one or more embodiments, the solid oral dosage form is formulated to achieve an immediate release profile, an extended release profile, or a delayed release profile. In one or more embodiments, the release profile of the solid oral dosage form is determined by using specific excipients that serve for example as binders, disintegrants, fillers, or coating materials. In one or more embodiments, the composition is formulated to achieve a particular time release profile as known to one skilled in the art. One or more embodiments incorporate controlled- or sustained-release lipophilic coatings (e.g. fatty acids, waxes, oils).

EXAMPLES OVERVIEW

A series of clinical studies and animal experiments were performed to demonstrate aspects of the invention. These are described in the subsequent sections.

Example 1 describes a single-dose human clinical study of a tablet that generates molecular iodine in the stomach. The results show that peak plasma concentration of total iodine occurs in less than 120 minutes, which indicates that the molecular iodine is absorbed from the stomach and not from the intestines. This experiment also shows that the area under the curve at 24 hours (i.e., AUC(0-24 h)) for serum concentration of total iodine is linear with dose.

Example 2 describes a single-dose human clinical study of a tablet that generates molecular iodine in the stomach for subjects who have either fed or fasted prior to ingestion of the tablet. The study shows (1) total iodine in plasma reaches a lower peak concentration and (2) the peak concentration is achieved later if food is present in the stomach than if food is not present. This indicates that molecular iodine does bind to organic molecules, such as vitamin A and D, within the stomach.

Example 3 is a laboratory experiment that demonstrates that vitamin D is iodinated in simulated gastric fluid (SGF).

Example 4 is a laboratory experiment that demonstrates that vitamin A is iodinated in simulated gastric fluid (SGF).

Example 5 is a laboratory experiment that demonstrates the importance of a homogeneous distribution of iodide and iodate to achieve the highest ratio possible of molecular iodine to total iodine from a mixture of iodide and iodate.

Example 6 is a 14-day rat study that shows there is a linear dose response for plasma concentration of total iodine as a function of generated molecular iodine.

Example 7 is a 90-day rat study that, in combination with the data from Examples 1 and 6, identifies the dosage equivalent for molecular iodine between rats and humans. This equivalence, plus safety data from Example 6 are used to set an upper dosage level for iodine within the solid oral dosage form.

Example 8 is a study for rats that are given diets that are deficient in one or more of iodine, iron, calcium, and selenium. Rats receive molecular iodine dosages in this experiment.

Example 1

Single Dose Study in Humans of Dosage Form Effective to Release Molecular Iodine in the Stomach An experiment was performed that confirmed that molecular iodine is rapidly absorbed by humans from gastric fluid before the iodine can reach the lower gastrointestinal (GI) tract.

A single-center, open-label, randomized, crossover design study was conducted in 18 healthy, female volunteers aged 18 to 45. The study was conducted with the oversight of an accredited institutional review board (IRB). The IRB approved the informed consent prior to initiation of the study. Written informed consent was obtained from each subject prior to performing any evaluations for that subject. Each subject received a sequence of three single-dose treatments under fasted conditions over a period of 3 weeks. A solid dosage form that delivers molecular iodine to the stomach was administered as single doses of 1.5, 3.0, and 6.0 mg. Administration occurred once weekly for 3 weeks with a 7-day wash-out period elapsed between doses. Plasma samples were drawn at baseline and then for 48 hours after administration.

Iodine values were measured with a validated, inductively coupled, plasma mass spectrometer. Serum iodide concentrations were corrected for the pre-dose serum iodine values. The following pharmacokinetic variables were calculated: the area under the curve (AUC) for total iodine; the maximum plasma concentration (Cmax) of plasma total iodine; the time to Cmax (Tmax); the elimination half-life (t½) of plasma total iodine; and the change from baseline in the 24-hour urinary excretion of total iodine.

Serum total iodine concentrations were corrected for baseline by subtracting the baseline ("time 0") concentration from that for each subsequent sample—the baseline corrected concentrations were used in all pharmacokinetic calculations along with actual blood sampling times. For graphical presentation of mean data, nominal times were used in the calculation of mean serum concentrations. All pharmacokinetic calculations were done using the SAS software package (SAS Institute, Inc., Cary, N.C.).

The results of this experiment are shown in FIG. 1. The mean of the maximum serum concentration (Cmax) measurements was less than 120 minutes for all three doses. This rapid absorption means that iodine is systemically absorbed from the stomach before passing into the lower intestinal tract which is a preferred formulation design since once molecular iodine transits to the lower GI tract it will be rapidly hydrolyzed and converted into iodide and hypoiodious acid, thus making it unavailable in the form of molecular iodine. This rapid absorption was observed for all three dose levels. Cmax varied linearly as a function of dose. The mean of the AUC at the maximum time point was approximately twice as large for those subjects receiving the 6.0 mg dose in comparison to the corresponding mean AUC at the maximum time point for those subjects receiving the 3.0 mg dose. Similarly, the mean of the AUC at the maximum time point was approximately four times as large for those subjects receiving the 6.0 mg dose in comparison to the corresponding mean AUC for those subjects receiving the 1.5 mg dose. These data are consistent with a linear response in AUC at the maximum time point as a function of dose. The mean observed half-life was approximately 422 minutes and there were no significant differences among doses with respect to excretion rates (p=0.152). Taken as a whole, the plasma concentration and urinary excretion data indicate that the proportion of the ingested iodine that was absorbed into the plasma was independent of dose over the range of 1.5 to 6.0 mg.

Example 2

Single Dose Study in Humans of Dosage Form Effective to Release Molecular Iodine in the Stomach—Differences in Administration in a Fasted Versus a Fed-State A second human clinical study was conducted to demonstrate that molecular iodine in gastric fluid reacts with organic molecules, like vitamins A and D.

Twenty-four healthy, non-smoking female volunteers completed the study. The volunteers ranged in age from 21 to 40 years old. The study was conducted with the oversight of an accredited institutional review board (IRB). The IRB approved the informed consent prior to initiation of the study. Written informed consent was obtained from each subject prior to performing any evaluations for that subject.

The study utilized a randomized, four-way, crossover design in which all subjects ingested 2 capsules that contained molecular iodine. Subjects ingested capsules under fed and fasting conditions. A seven-day washout period was used between interventions under the fed and fasting conditions. Blood was drawn and urine collected for 48 hours following ingestion of each capsule. The experiment was repeated with two lots of the capsules: lot FP and lot PP. Each capsule in lots FP and PP contained 3 mg of molecular iodine. The FP and PP lots differed slightly in the excipient ingredients that were included in the solid oral dosage form. The study was conducted under the supervision of Albert Cohen, M.D. in the facilities of Peninsular Testing Corporation, Miami, Fla. The intervention groups are shown below.

Intervention 1: fasting condition, lot PP 2 capsules
Intervention 2: fed condition, lot PP 2 capsules
Intervention 3: fasting condition, lot FP 2 capsules
Intervention 4: fed condition, lot FP 2 capsules Plasma and urine samples were assayed for total iodine by inductively coupled plasma mass spectrometry using a validated assay (Mayo Clinic Division of Clinical Biochemistry and Immunology Metals Laboratory in Rochester, Minn.).

Blood samples were collected during the 24 hours prior to the first intervention period in order to obtain baseline plasma concentrations of iodine in the volunteers used in the study. The blood samples were drawn at approximately 8 AM, 12 PM (noon), 8 PM, 12 AM (midnight) and 8 AM and were labeled as −24, −20, −12, −8, and 0 hours, respectively. The last sample, 8 AM or 0 hours, was collected immediately before the first dose of the capsule. These samples were assayed for total iodine. Since a baseline or 0-time value was available for each subject before each intervention, this baseline value was used for baseline adjustment of the individual plasma concentration data obtained for each intervention.

A total of 4 study groups were used; two groups of subjects (fed and fasted) with both the PP and FP capsule lots. Subjects were dosed at 8:00 AM on day 0. Subjects in the fasted groups were permitted a light snack at 10:00 PM on the evening prior to day 0 but remained fasting until 4 hours after the 8:00 AM dose of the study capsules. Subjects in the fed groups were permitted an identical light snack at 10:00 PM on the evening prior to the study and also received a standardized breakfast consisting of one Egg McMuffin (or item of equivalent caloric and fat content), one hash brown patty, 6 fluid ounces orange juice, and 8 fluid ounces whole milk which was to be ingested over 15 minutes beginning at 7:40 AM on the day of study (day 0). Five minutes after completion of the breakfast (8:00 AM), subjects in the fed groups ingested the assigned study capsules, from either the PP or FP lot.

The mean Cmax values for iodine were nearly identical for the two different lots, PP and FP, when dosed under similar conditions. The fasting mean Cmax (±standard deviation) was 425.2±186.1 ng per ml for the PP lot and 420.5±20.23 ng per ml for the FP lot. When the capsules were administered after a high fat breakfast, the mean Cmax values were 309.5±235.6 and 302.5±34.2 ng per ml for the PP and FP lots, respectively. The Cmax parameters obtained when doses were administered fasting were statistically greater (p=0.001) than those obtained after a meal. Additionally, for both solid oral dosage forms, Tmax was shorter for doses administered fasting, which indicates that the greater Cmax for fasting subjects was due to delivery of molecular iodine in the stomach and interactions of the food in the stomach with molecular iodine reduces the amount of molecular iodine absorbed via the stomach.

The data demonstrate, unexpectedly, that iodine is absorbed into the blood more slowly and with a lower peak concentration when delivered in the presence of organic food material in the gastric fluid of the GI tract. This indicates that molecular iodine binds to organic food material in the gastric fluid, thus making it unavailable for absorption via the stomach. For this reason, it is preferred that the solid oral dosage form be taken on an empty stomach. Additionally, to increase beneficial uptake of molecular iodine from the solid oral dosage form via the stomach, ingredients that can be beneficially absorbed from the intestines rather than the stomach can be coated with an enteric coating to prevent reaction with molecular iodine in the stomach.

Example 3

Investigation of Interaction Between Vitamin D and Molecular Iodine in Gastric Fluid An experiment was conducted to determine whether vitamin D is iodinated by molecular iodine in gastric fluid.

Test solution 1 was produced according to the following procedure. Two grams (2.0 g) of molecular iodine crystals were added to a 1-liter volumetric flask with a glass stopper; the volumetric flask was filled to the 1-liter mark with simulated gastric fluid (SGF) and a stir bar was then added to the flask; the solution was stirred for four hours to allow molecular iodine to saturate the SGF. The resulting mixture is called the molecular iodine-SGF mixture. A solution was produced by mixing 2.0 ml of a vitamin D3 solution (100 µg/ml in ethanol (EtOH), Sigma-Aldrich Corp., St. Louis, Mo., Sigma Cat. No. 740292) into 40 ml of the molecular iodine-SGF mixture in a 50 ml volumetric flask with a glass stopper. A stir bar was then added to the flask and the solution was stirred for 10 minutes to form test solution 1.

Control solution 1 was produced as follows. A solution was produced by mixing 2.0 ml of a vitamin D3 solution (100 µg/ml in ethanol) into 40 ml of SGF in a 50 ml volumetric flask with a glass stopper. A stir bar was then added to the flask and the solution was stirred for 10 minutes to form control solution 1. Control solution 1 contained about 4.8 µg/ml of vitamin D3.

Test solution 1 and control solution 1 were then analyzed using reverse phase chromatography at 25° C. (Sigma-Aldrich Corp., St. Louis, Mo., C18 Sigma-Aldrich Ascentis Express, 25 centimeter (cm) length and 4.6 millimeter (mm) interior diameter, Cat. No. 53825-U) with acetonitrile:methanol 8:2 (2.0 ml per minute) as the mobile phase and a refractive index detector (Series 200 Refractive Index Detector, Perkin Elmer, Norwalk, Conn.) for detection. For each chromatography measurement, the column was equilibrated with the mobile phase for 30 minutes. The sequence of chromatography measurements was (1) mobile phase, (2) control solution 1, (3) mobile phase, (4) test solution 1, (5) mobile phase, (6) test solution 1, (7) mobile phase, and (8) control solution 1. For each chromatography measurement, the elution time was evaluated for the analytes. Control solution 1 allowed clear identification of the elution time that corresponds to vitamin D3, which was 14.3 minutes; a smaller $2^{nd}$ peak was also present at 13.7 minutes which was ascribed to vitamin D2. For test solution 1, the elution time peaks at 13.7 and 14.3 minutes were shifted to a series of peaks with elution times that ranged from 10.9 to 12.6 minutes.

The differences in peaks and elution times observed in this experiment demonstrate, unexpectedly, that molecular iodine iodinates vitamin D in gastric fluid.

Thus, a reaction between molecular iodine and vitamin D in the stomach, unexpectedly, reduces the amount of molecular iodine that is available to be absorbed from the stomach and the amount of vitamin D that is present to be absorbed from the intestines.

Example 4

Investigation of Interaction Between Vitamin A and Molecular Iodine in Gastric Fluid An experiment was conducted to determine if vitamin A is iodinated by molecular iodine in gastric fluid. Retinoic acid was used as a proxy for vitamin A since the two molecules differ only in the oxidation state of the hydroxyl group at position 1 which will not influence the reaction of these two molecules with molecular iodine.

An 8.3 millimolar (mM) solution of stock retinoic acid was prepared daily in a dark room by dissolving retinoic acid (Sigma R2524) in 95% ethanol at room temperature; the mixture was vortexed until the retinoic acid was completely dissolved and then a TEFLON-lined screw cap was placed on the vial and the vial wrapped in aluminum foil and placed in a refrigerator until required. Prior to analysis the 8.3 mM stock solution of retinoic acid was (1) diluted to a concentration of 8 micromolar in either (a) molecular iodine-SGF containing 5% ethanol (test solution 2) or (b) SGF containing 5% ethanol (control solution 2); (2) allowed to incubate in closed vial for 10 minutes at 37° C.; and (3) analyzed to determine the presence of retinoic acid.

Test solution 2 and control solution 2 were then analyzed using normal phase chromatography at room temperature column (150×2 mm; 5 micrometer particle size) (Inertsil, Keystone Scientific Inc., Bellefonte, Pa.). They were eluted (flow rate 0.2 ml/min) with an 18.9 minute linear gradient from 90% solvent A (hexane) and 10% solvent B (hexane-dioxane-isopropanol, 40:8:2) to 58% solvent A and 42% solvent B. The sequence of chromatography measurements was (1) mobile phase, (2) control solution 2, (3) mobile phase, (4) test solution 2, (5) mobile phase, (6) test solution 2, (7) mobile phase, and (8) test solution 2.

Control solution 2 samples consistently demonstrated multiple peaks with elution times between 7.8 and 8.8 minutes. The peak elution times for test solution 2 were consistently longer than those observed for control solution 2, which ranged from 12.5 to 16.1 minutes. The elution of test solution 2 demonstrated a multiplicity of peaks as compared to the elution of control solution 2 and many of these peaks were asymmetric and broadened in contrast to those of control solution 2.

The differences in peaks and elution times observed in this experiment demonstrate, unexpectedly, that molecular iodine iodinates vitamin A in gastric fluid.

Thus, a reaction between molecular iodine and vitamin A in the stomach unexpectedly reduces the amount of molecular iodine that is available to be absorbed from the stomach and the amount of vitamin A that is present to be absorbed from the intestines.

Example 5

Impact of Distribution of Formulation Components in the Solid Dosage Form

This experiment demonstrates the importance of a homogeneous distribution to achieve the highest ratio possible of molecular iodine to total iodine of a mixture of iodide and iodate. To maximize the ratio of molecular iodine to total iodine, iodide and iodate were mixed in a molar ratio of 5:1.

Iodide levels were measured using an iodide-selective electrode (Nova Analytics Corp., Woburn, Mass.; Catalogue No. 476127) calibrated against concentration using standards prepared from analytical-grade sodium iodide. Free molecular iodine was measured by a potentiometric method (Gottardi, W., Fresenius Z. Anal. Chem. Vol. 314, pp. 582-585, 1983) which relies upon measurement of the iodide activity and the redox potential. Iodide activity was measured using an iodide ion selective electrode calibrated against standards with known activity, and the redox potential was measured with a platinum electrode (Fisher Scientific Company, LLC, Pittsburgh, Pa.; Fisher Catalog No. 1 3-620-1 15) calibrated with an iodine-iodide redox buffer. A Fisher reference electrode (Fisher Scientific Company, LLC, Pittsburgh, Pa.; Fisher Catalog No. 13-620-51) and Corning Model 345 pH meter (Nova Analytics Corp., Woburn, Mass.) were used for potentiometric measurements.

A 250 ml cylindrical screw top bottle with a TEFLON-lined lid was used for this experiment. Two holes were drilled through the screw top lid. The diameter of one hole was sized to fit an iodide ion selective electrode; the other hole was sized to fit a platinum electrode. A third hole was drilled to allow reagent to be added to or removed from the bottle.

For the first experiment, a mass of 79.50 mg of sodium iodide and 20.99 mg of sodium iodate were weighed out into separate weighing boats. These two powders were then deposited on the bottom of the 250 ml cylindrical bottle at opposite sides of the bottle such that the materials did not contact each other. The screw top lid was then closed on top of the bottle. One hundred ml of 1 normal hydrochloric acid was added to the bottle and the bottle was shaken one time every 5 minutes. The solution was periodically mixed until all of the powder was dissolved. Once completely dissolved the observed concentration of molecular iodine was 71 ppm.

For the second experiment, a mass of 79.50 mg of sodium iodide and 20.99 mg of sodium iodate were weighed into a pestle and were then homogenized using a mortar to blend these two materials. The blended powders were then deposited across the bottom of the 250 ml cylindrical bottle. The screw top lid was then closed and 100 ml of 1 normal HCl was added to the bottle and the bottle was shaken one time every 5 minutes. The solution was periodically mixed until all of the powder was in solution. Once completely dissolved the observed concentration of molecular iodine was 103 ppm. It was unexpected that the results were over 40% higher when mixed in a homogenous distribution than when dissolved in a non-homogenous manner.

This pair of experiments demonstrates the unexpected importance of incorporating a homogeneous mixture of a defined ratio of iodide to iodate in the active component of a solid oral dosage form.

Example 6

Administration of Solid Dosage Form in Rats—14 Day Study

Example 1 studied human subjects receiving a solid dosage form that formed molecular iodine in the stomach. That Example established that serum levels are linearly related to the dose contained in the solid dosage form. An additional experiment (this Example) was performed to determine whether the linear dose proportionality of serum iodine levels is similarly observed in rats. By showing that the linear dose proportionality is observed in rats, this Example showed that rats are an appropriate model for studying preferred concentrations of nutrient ingredients directed to reducing thyroid-related adverse events when orally administering an iodine solid oral dosage form that delivers supraphysiological levels of iodine by forming molecular iodine in the stomach.

Dose proportionality of serum levels of iodine was established in rats was established in this study. In addition, comparison of total iodine in serum of rats dosed with 10 mg per kg per day of either iodide or molecular iodine suggested that orally administered iodine is cleared from serum more rapidly administered as iodide which is consistent with the data in the fed and fasted human study described in Example 2.

Twelve female rats per group were administered 0.1, 1, or 10 mg per kg per day of molecular iodine once daily by oral gavage for 14 consecutive days. One additional group of 12 female rats (iodide control group) received 10 mg per kg per day of iodide. The iodide control group was included since fed and fasted studies in humans (Example 2) demonstrated that orally administered molecular iodine reacts with organic material and therefore is excreted more slowly from the body; this suggested that serum levels of the iodide control group should be lower than the 10 mg per kg per day molecular iodine treatment group since iodide doesn't react with organic matter and therefore should be systemically cleared more rapidly that orally administered molecular iodine. An additional 12 female rats (controls) received deionized water.

All clinical aspects of this study were conducted at ITR Laboratories Canada, Inc. (ITR) (Baie d'Urfe, Quebec, Canada). The test article consisted of sodium iodate (Ajay North American, LLC, Lot 030496) and USP sodium iodide (West Agro, Cat. No. 9008-047, lot 197). Two test solutions were prepared as follows: (1) adding 660 mg of sodium iodate (test article Group A) to a 1-liter screw-top plastic bottle and sealing the bottle and (2) adding 1500 mg of sodium iodide (test article Group B) to a 1-liter screw-top plastic bottle and sealing the bottle. ITR reconstituted one set of test articles (1 from Group A and 1 from Group B) and used these reconstituted test articles for the entire 14 day study. ITR gavaged a 1:1 mixture of the test articles to rats.

The test articles were analyzed during the testing period and for a time that extended beyond the testing period to ensure stability. Titratable iodine concentrations were measured via titration with sodium thiosulfate. The titrations were performed in triplicate. Iodide was measured separately using an ion-selective electrode (ISE—Corning Model 476127, SN XT100300; Reference—Accumet Model 13 620 51, SN 5048167; Corning pH Meter 345, SN C1117R). Measurements were made on days 2, 3, 5, 8, 11 and 15 following reconstitution of test articles from Group A and Group B. The test articles were stable throughout the study based on iodide and titratable iodine measurements.

All animals survived until termination of treatment. There were no statistically significant clinical signs that could be related to treatment. There was no statistically significant effect of treatment on animal body weights throughout the course of the study.

There was a dose-related increase in the serum levels of iodine in the serum of treated animals as observed in humans. The concentration of serum iodine in the treatment group that received iodide was unexpectedly lower than the treatment group that the corresponding concentration of molecular iodine (10 mg per kg per day). Unexpectedly, there was no statistically significant difference in serum levels of TSH, T4, or T3 (see results in Table 2).

TABLE 2

Clinical Chemistry Results at Test Completion

| Dose | Clinical Chemistry Determinations | | | |
|---|---|---|---|---|
| mg/kg/day | Iodine µg/dl | TSH µU/ml | $T_4$ µg/dl | $T_3$ ng/dl |
| 0 | 10.6 ± 2.5 | 29.4 ± 4.9 | 3.26 ± 0.70 | 80.43 ± 20.6 |
| 0.1 | 22.8 ± 5.7 | 29.2 ± 6.0 | 3.23 ± 0.59 | 81.13 ± 11.1 |
| 1.0 | 138.7 ± 21.2 | 31.0 ± 8.4 | 3.42 ± 0.89 | 75.23 ± 21.3 |
| 10.0 | 1176.3 ± 249.3 | 33.3 ± 7.6 | 3.20 ± 0.79 | 78.73 ± 18.7 |
| 10.0 as iodide | 982.4 ± 332.1 | 31.1 ± 4.6 | 2.87 ± 0.55 | 79.36 ± 16.9 |

Example 7

Administration in Rats—90 Day Study

A 90-day study of a test article (sodium iodide and sodium iodate in a solution of sodium carbonate) was conducted. The study consisted of two sub-studies. The first sub-study looked at the maximum safe dosage level for rats. The second sub-study provided a basis to compare the pharmacokinetic characteristics of molecular iodine in rat to those for humans. The study was conducted in order to design studies relevant to humans for evaluation of ingredients that are directed to reducing thyroid related adverse events when orally administering an iodine solid oral dosage form that delivers supraphysiological levels of iodine by forming molecular iodine in vivo.

The study was conducted at Charles River Laboratories in Worcester, Mass. Sprague-Dawley rats (101 male and 101 nulliparous and non-pregnant female) from Charles River Laboratories, Kingston, N.Y. were received at six weeks of age and were examined for signs of disease or injury upon receipt. The animals were allowed to acclimate to laboratory conditions for seven days. No abnormal findings excluding animals from study were noted. The animals were released from conditioning following an examination by the attending clinical veterinarian. Each animal was identified with a unique number that was indicated by ear punch. Cage labels, color-coded by group, identified each cage with study number, group number, sex, species, and individual animal identification number. Animals were randomized into treatment groups by weight. At randomization, the weight variation of animals did not exceed ±20% of the mean weight.

The animals were individually housed in stainless steel cages. Environmental controls were set to maintain a temperature of 18 to 26° C. and a relative humidity of 30 to 70%. A 12-hour light/dark cycle was employed and the room underwent a minimum of ten fresh air changes per hour. The concentrations of calcium, iron, and selenium in the feed were 0.80%, 220 ppm, and 0.30 ppm, respectively. The animals were fed LABDIET Certified Rodent Chow 5002 (PMI Feeds, Inc., St. Louis, Mo.) ad libitum and were provided fresh filtered tap water ad libitum. The feed was analyzed by the manufacturer for concentrations of specified heavy metals, aflatoxin, organophosphates, and for selenium, calcium and iron.

Placebo (control test articles) only contained sodium carbonate. To prepare the test article, 7.0 liters of deionized water and 20 g of sodium carbonate were combined in a calibrated container and mixed until the sodium carbonate was dissolved. Additional deionized water was added to yield a final volume of 10.0 liters.

The active test article contained 196.86 g of sodium iodide (Lot 3667, West Agro Inc., Kansas City, Mo.), 51.96 g of sodium iodate (Lot 070997, Ajay North America, Powder Springs, Ga.) and 4.0 g of sodium carbonate (Lot T32146, J. T. Baker, Phillipsburg, N.J.). The active test article was reconstituted to a final volume of 2.0 liters with water prior to use. When reconstituted in 2 liters of water, the concentration of active iodine was equivalent to 100 mg/ml of molecular iodine.

Rats were dosed with the following concentrations: 0.0 mg/ml (Group 1), 0.4 mg/ml (Group 2), 2.0 (Group 3), and 50 mg/ml (Group 4). Test articles for each group were prepared by dilution of the active test article with the control test article. The resulting active test articles were reconstituted at the start of each week and stored throughout the week at room temperature. Rats were dosed at a volume of 10 ml per kg of body weight. Throughout the study, the test article was stable in pH and in the concentration of both iodide and iodine.

The first sub-study consisted of four groups of ten male and ten female rats. Rats in Group 1 received the vehicle control (sodium carbonate) by daily gavage for 90 days. Rats in Groups 2, 3, and 4 were administered gavage doses of 4, 20, or 500 mg/kg of molecular iodine, respectively, once daily for 90 days. Each group of ten rats was necropsied on Day 91. An experiment with a daily dose of 1000 mg/kg showed that this level was not safe for rats.

Clinical observations, ophthalmic examinations, body weights, food consumption measurements, clinical pathology (hematology, blood coagulation, serum chemistry, and urinalysis), organ weights, and assessment of anatomic pathology were conducted during the study. In addition, serum levels of thyroid stimulating hormone (TSH), tri-iodothyronine (T3), and thyroxine (T4) were analyzed in serum collected on Days 91.

Blood for clinical pathology and hormone analysis was collected by puncture of the abdominal aorta/vena cava after the animals were anesthetized with a mixture of ketamine, xylazine, and acepromazine. Following collection, samples were transferred to an appropriate laboratory for processing and analysis. Blood samples were processed and the parameters specified in Table 3 were determined using a Boehringer Mannheim Hitachi 717 chemistry analyzer or with an Perkin Elmer-Agilent 7500 ICP-MS.

TABLE 3

Serum Chemistry Parameters Measured

| | | |
|---|---|---|
| Glucose (GLU) | Potassium (K) | Triglycerides (TRG) |
| Urea nitrogen (BUN) | Selenium (Se)[b] | Creatinine (CRE) |
| Total protein (TPR) | Chloride (CL) | Total bilirubin (TBIL) |
| Albumin (ALB) | Calcium (CAL) | Aspartate aminotransferase (AST) |
| Globulin (GLOB)[a] | Phosphorus (PHOS) | |
| Albumin/Globulin ratio (A/G)[a] | Alanine aminotransferase (ALT) | Alkaline phosphatase (ALK) |
| Sodium (Na) | Total cholesterol (CHOL) | Gamma glutamyltransferase (GGT) |
| Iron (Fe)[b] | Creatinine Kinase (CK) | |

[a]Calculated value.
[b]ICP-MS.

Blood samples for thyroid hormone analysis were centrifuged, and the serum was extracted, transferred into labeled tubes, and stored frozen at −70° C. The hormone analysis for TSH, $T_3$, and $T_4$ in serum was conducted under Good Laboratory Practice at Analytics Laboratories, Gaithersburg, Md.

A comprehensive necropsy, defined as the macroscopic examination of the external surface of the body, all orifices, and the cranial, thoracic, and abdominal cavities and their contents, was performed on all rats in the first sub-study. Organs and tissues were dissected free and fixed in 10% neutral buffered formalin, except for the eyes, which were fixed in Davidson's solution. Observations noted at necropsy were recorded.

The results from the first sub-study unexpectedly showed that the maximum dose of 500 mg per day per kg of body weight was a safe dose and that 1000 mg per day per kg of body weight was an unsafe dose.

The second sub-study was the pharmacokinetic portion of the study. This sub-study used a separate set of rats from the first sub-study. Six males and six female rats were used with the control vehicle; 12 male and 12 female rats were used for each dose group (i.e., Groups 2, 3 and 4). At specified time points on Days 1 and 91, blood was collected for analysis of serum iodine levels. Pharmacokinetic parameters were calculated for serum iodine concentrations on Days 1 and 91.

Blood samples for pharmacokinetic sub-study were collected by puncture of the retro-orbital sinus/plexus after the animals were anesthetized with $CO_2$. Blood samples were obtained on Days 1 and 91. On each of Day 1 and Day 91, blood was collected from groups of three rats of each sex at predose, 4, and 12 hours post treatment and three rats of each sex at 2, 8, and 24 hours post treatment. These rats were euthanized following the 12-hour or 24-hour blood collection, respectively. Only Day 1 analysis included rats in Group 1. The analysis for Day 1 and Day 91 included Groups 2, 3, and 4. Background levels of total iodine at Day 91 were based on the blood samples obtained from Group 1 at Day 1. Following collection, samples were centrifuged and serum was extracted and transferred to labeled tubes and frozen at −20° C. These samples were then analyzed using a validated method.

Figure 2:
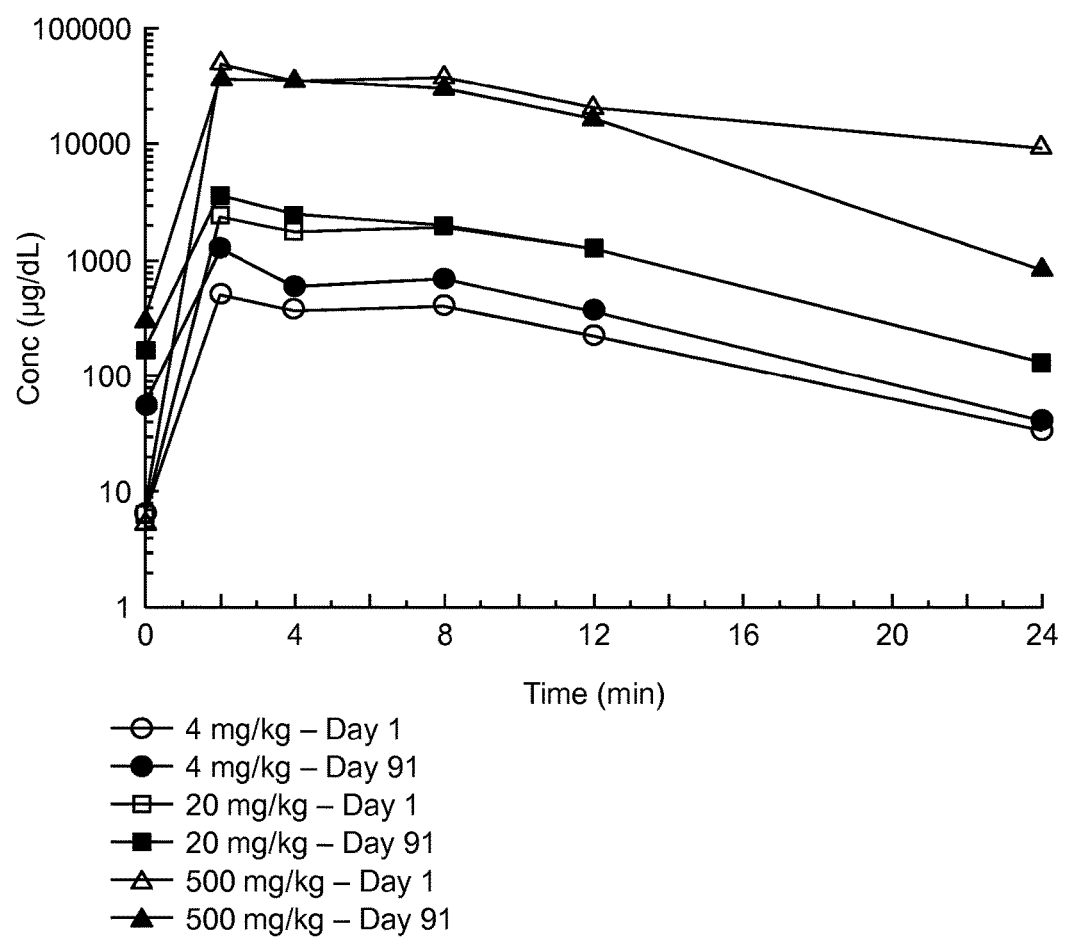
FIG. 2 is a graph of mean serum concentration of total iodine in blood in a study carried out on Sprague-Dawley rats. Mean serum levels are plotted as a function of time based upon each rat's most recent oral dosing as described in Example 7.

Total iodine levels for Groups 2, 3, and 4 on Day 1 and Day 91 are plotted in FIG. 2 as a function of time since the most recent dose. The rats whose results are described in FIG. 2 were dosed daily for a 90-day period with a test article comprising sodium iodide and sodium iodate in a sodium carbonate solution. The dosage for each rat was designed to create molecular iodine in an acidic environment. Four groups were studied, corresponding to doses of 0, 4, 20, and 500 mg of molecular iodine per kg of body weight per day.

Example 1 measured the human AUC(0-24 h) for total serum iodine after a single 6 mg dose as 2.9 μg·hr/ml (17,451±3,090 μg·min/dl). Example 5 demonstrated a Cmax of 1.29 μg/ml for total serum iodine in rats at the Tmax of 2 hours. The second sub-study of Example 7 demonstrated a half-life in rats of approximately 12 hours. Combining these values from Examples 6 and 7, produces an estimate of the AUC(0-24 h) of 19 μg·hr/ml which is 6.6 times the human AUC(0-24 h). From this data, a dose of 0.152 mg of iodine per day per kg of body weight can be extrapolated to be equivalent to a 6 mg daily dose in human.

Based on the results of sub-study 1, the maximum safe dosage for rats was determined unexpectedly to be 500 mg per day per kg of body weight. This corresponds to a human dose of approximately 20,000 mg per day, which was unexpected. To achieve a safety factor in excess of 300, a maximum dosage for humans of approximately 60 mg per day is recommended.

Example 8

Administration of Solid Dosage Form Comprising Metal Ions in Rats: Demonstration of Synergistic Effects Among Calcium, Iron and Selenium in Achieving Normal Thyroid Function Following Administration of Molecular Iodine To demonstrate the individual and synergistic effects of the ingredients described herein, a study is performed in rats. The risk of thyroid related adverse event in response to chronic supraphysiological iodine administration is related to nutritional status. For instance, it is well known that iodine-deficient populations experience an elevated rate of thyroid-related adverse events compared to iodine sufficient populations. The rat model established in Examples 6 and 7 of this application (supra) can be used to demonstrate the synergistic effects of added selenium, calcium, and iron. The study compares the levels of the thyroid hormones TSH, T3, and T4 with a goal of achieving normal thyroid function.

In this Example, 170 Sprague-Dawley rats (85 male and 85 nulliparous and nonpregnant female) (Charles River Laboratories, Kingston, N.Y.) are received at six weeks of age and examined for signs of disease or injury. The animals are randomly assigned to 17 groups (Groups 1-17), with each group consisting of 5 male and 5 female rats.

Upon arrival at the lab, all animals are maintained on the AIN-93M diet (Nutrient Requirements of Laboratory Animals, Fourth Revised Edition, 1995; ISBN: 0-309-58849-9) for seven days and allowed to acclimate to laboratory conditions. All rat diets for this Example are given in pellet form (Dyets, Inc., Bethlehem, Pa.) ad libitum.

At the end of day 7, animals in all groups except for Group 1 (the control group) are switched to a diet deficient in iron, selenium, calcium, and iodine ("Deficient Diet") for the next 4 weeks ("Deficiency Period"). The Deficient Diet is the AIN-93 diet modified by not including ingredients containing selenium or iodine and further modified as described by Medeiros, et al. J. Nutr. 132: 3135-3141, 2002 to create a diet that is deficient in iron and calcium. During the Deficiency Period, Group 1 is maintained on the AIN-93M diet, which contains baseline levels of iron, selenium, calcium, and iodine.

At the end of the 4-week Deficiency Period, all animals are switched to the treatment diets described in Table 4 for a Treatment Period lasting 4 weeks. The levels of ingredients in Table 4 (i.e., "Deficient," "Low," etc.) correspond to ingredient concentrations as described in Table 5 for each of the ingredients.

During the Treatment Period, rats in Groups 2 to 16 are gavaged daily with a solution that contains a mixture of iodide and iodate that forms molecular iodine when added to simulated gastric fluid. Groups 1 and 17 are gavaged with a similar solution that did not contain iodide and iodate. Rats in Groups 2 to 16 are dosed with the equivalent of 0.15 mg of iodine per kg of body weight daily; results of Example 7 established an equivalence of 0.152 mg of iodine per kg of body weight in rats to 6 mg of molecular iodine per day for humans.

TABLE 4

Rat treatment diets during the Treatment Period.

| Treatment Group | Selenium | Iron | Calcium |
|---|---|---|---|
| 1 (control) | AIN-93M | AIN-93M | AIN-93M |
| 2 | High | High | High |
| 3 | High | High | Deficient |
| 4 | High | Deficient | High |
| 5 | High | Deficient | Deficient |
| 6 | Deficient | High | High |
| 7 | Deficient | High | Deficient |
| 8 | Deficient | Deficient | High |
| 9 | Low | Low | Low |
| 10 | Low | Low | Deficient |
| 11 | Low | Deficient | Low |
| 12 | Low | Deficient | Deficient |
| 13 | Deficient | Low | Low |
| 14 | Deficient | Low | Deficient |
| 15 | Deficient | Deficient | Low |
| 16 | Deficient | Deficient | Deficient |
| 17 | Deficient | Deficient | Deficient |

AIN = AIN-93M diet
Deficient = Deficient Diet Level
Low = Low Diet Level
High = High Diet Level

TABLE 5

Ingredient concentrations for diet levels referenced in Table 4.

| | mg of ingredient per kg of feed | | | |
| Ingredient | AIN-93 diet | Deficient Diet Level | Low Diet Level | High Diet Level |
|---|---|---|---|---|
| Selenium (in the form of sodium selenite) | 0.15 | 0.015 | 0.10 | 0.15 |
| Iron (in the form of ferric citrate) | 35 | 5 | 15 | 35 |
| Calcium (in the form of anhydrous calcium carbonate) | 5000 | 250 | 3000 | 5000 |
| Iodine (in the form of potassium iodate) | 0.21 | 0.021 | 0 | 0 |

The study compares the levels of the thyroid hormones TSH, T3, and T4 with a goal of achieving normal thyroid function. The key metrics for this experiment are (1) normalization of thyroid function and (2) time to normalize thyroid function.

A preliminary experiment was conducted to evaluate the measurement process for obtaining TSH, T3, and T4 values. Thyroid status was monitored by measuring TSH. TSH was measured using an immunoassay (IBL International, Toronto, ON, Cat. No. SY45021) that required only 10 µl of sample. T3 and T4 were measured using a multiplex immunoassay that required 25 µl of sample (Millipore, Waltham, Mass., Cat. No. RTHY-30K-T3T4, Rat Thyroid Hormone T3/T4 Panel-2 Plex-Endocrine Multiplex Assay). The back of the leg of each rat was shaved with an electric trimmer until the saphenous vein was clearly visible. While one person restrained the rat, a technician punctured the vein using a 22 G needle and collected between 75 and 100 µl of blood into a microcentrifuge tube (Eppendorf North America, Inc. Hauppauge, N.Y., Cat. No. 022363611) every other day. Samples were allowed to clot, spun for 10 minutes at 2,000 times the gravitational constant and frozen at −20° C. TSH, T4, and T3 values were determined on all samples after thawing at the end of the study. Results were analyzed for male and female rats separately since there is a significant difference between the two populations. The mean TSH, T3, and T4 values for the male group (n=5) were: 0.804±0.293 ng/ml; 37.02±11.87 ng/dl and 3.69±0.793 ng/dl respectively as compared to 1.49±0.298 ng/ml; 73.78±15.63 ng/dl and 1.658±0.554 ng/dl for the female group (n=5).

The mean and standard deviation for each treatment group was calculated. The normal range thyroid function for males was defined in this experiment as a TSH value that is within 2 standard deviation units of that measured for Group 1 males; the comparable normal range for females was established in an identical manner. For treatment groups the males and females were evaluated separately. A dietary regimen is scored as restoring normal thyroid function once the mean TSH values for both male and female rats in a treatment group were within 2 standard deviation units of their corresponding Control group. The time at which the dietary regimen restores normal thyroid function is also an important outcome for this Example since the sooner normal thyroid function is restored the less risk the animal experiences of an adverse thyroid related event.

The measurements of the Example follow the procedure of the preliminary experiment. In the Example, blood is drawn from each rat every 2 days during the Treatment Period and blood is frozen at −20° C. TSH, T4, and T3 values are determined on all samples after thawing at the end of the study.

Beneficial effects (i.e., normalization of thyroid function and/or faster normalization of thyroid function) are demonstrated based on these results. Synergistic effects among calcium, iron, and selenium are demonstrated, for example, by comparing the results for Groups 2, 3, 4, and/or 6 to the results for Group 16, which are deficient in calcium, iron, and selenium, and to the results from Groups 5, 7, and 8, which are given calcium, iron, or selenium individually. For example, the results from Group 6 are compared to the results from Groups 7, 8, and 16 to describe the synergistic effects of iron and calcium.

Minimum and maximum concentration levels for the cofactors are determined by adjusting the levels of each component in a standard design of experiments. An example of this is seen by comparing the results in the "Low" and "High" levels described in Groups 6 and 13 for calcium and iron.

It is claimed:

1. A solid oral dosage form, comprising
a source of iodine,
a reactive agent,
a metal ion selected from calcium and iron,
at least one vitamin selected from vitamin A and vitamin D, and
wherein
(i) the source of iodine is unreactive when in the solid oral dosage form,
(ii) the total iodine in the solid oral dosage form is 3 to 60 milligrams,
(iii) the source of iodine reacts with the reactive agent in simulated gastric fluid,
(iv) the solid oral dosage form, when placed in simulated gastric fluid for a period of up to 2 hours, generates a ratio of molecular iodine to total iodine in the range of 0.8 to 1.0 by weight, and
(v) the vitamin is physically separated from the source of iodine within the solid dosage form.

2. The solid oral dosage form of claim 1, wherein the reaction between the source of iodine and the reactive agent in (iii) is an oxidation-reduction reaction.

3. The solid oral dosage form of claim 1, wherein the ratio of the source of iodine to the reactive agent is within ±20% of the ideal ratio for creating a ratio of molecular iodine to total iodine within the range 0.97 to 1.0.

4. The solid oral dosage form of claim 3, wherein the source of iodine and the reactive agent are mixed in a homogeneous distribution within the solid oral dosage form.

5. The solid oral dosage form of claim 1, comprising 10 to 500 milligrams of calcium.

6. The solid oral dosage form of claim 5, comprising vitamin A.

7. The solid oral dosage form of claim 1, comprising 0.2 to 20 milligrams of iron.

8. The solid oral dosage form of claim 7, comprising vitamin D.

9. The solid oral dosage form of claim 1, further comprising selenium.

10. The solid oral dosage form of claim 9, wherein the solid oral dosage comprises iron.

11. The solid oral dosage form of claim 1, wherein the solid oral dosage form comprises calcium, iron, and selenium.

12. The solid oral dosage form of claim 11, comprising vitamin A and vitamin D.

13. The solid oral dosage form of claim 12, further comprising an enteric coating, wherein the enteric coating coats the vitamin A and the vitamin D.

14. The solid oral dosage form of claim 13, wherein the enteric coating coats no more than 20% of the source of iodine and the reactive agent.

15. The solid oral dosage form of claim 12, comprising a means for physically separating the vitamin A or vitamin D from the source of iodine within the solid dosage form.

16. The solid oral dosage form of claim 1, wherein
the source of iodine comprises iodide and
the reactive agent is selected from the group comprising an iodate salt, hydrogen peroxide, a source of iodate, and a source of hydrogen peroxide.

17. The solid oral dosage form of claim 16, further comprising a pH control agent such that the effective pH of the solid oral dosage form is between 7.0 and 12.0.

18. The solid oral dosage form of claim 1, wherein the source of iodine comprises iodide and the reactive agent is selected from the group comprising a ferric salt and a source of ferric iron.

19. The solid oral dosage form of claim 1, further comprising one or more ingredients selected from the group of gamma-linolenic acid, vitamin B1, magnesium, and zinc.

20. The solid oral dosage form of claim 1, wherein the total iodine in the solid oral dosage form is 6 to 50 milligrams.

21. The solid oral dosage form of claim 1, wherein the solid oral dosage form does not comprise selenium.

22. The solid oral dosage form of claim 1, wherein the solid oral dosage form does not comprise gamma-linolenic acid.

23. A solid oral dosage form, wherein the active ingredients consist of
an iodide salt,
an iodate salt, wherein the total iodine for all sources is 3 to 60 milligrams, and
one or more ingredients selected from the list consisting of
vitamin D,
vitamin A,
selenium,
iron, and
10 to 500 milligrams of calcium.

24. The solid oral dosage form of claim 23, wherein the one or more ingredients comprises iron and 1 to 30 micrograms of vitamin D.

25. The solid oral dosage form of claim 24, wherein the one or more ingredients comprises vitamin D and the dosage form further comprises an enteric coating material that coats the vitamin D and physically separates the vitamin D from either the iodide salt or the iodate salt.

26. The solid oral dosage form of claim 24, wherein the one or more ingredients comprises 25 to 100 micrograms of selenium.

27. The solid oral dosage form of claim 23, wherein the one or more ingredients comprises calcium and 10 to 1000 micrograms of vitamin A.

28. The solid oral dosage form of claim 27, further comprising an enteric coating material that coats the vitamin A.

29. The solid oral dosage form of claim 27, wherein the one or more ingredients comprises 25 to 100 micrograms of selenium.

30. The solid oral dosage form of claim 23, wherein the total iodine in the solid oral dosage form is 6 to 50 milligrams.

31. A method for treating fibrocystic breast condition comprising the steps of ingesting a solid oral dosage form that comprises 3 to 60 milligrams of iodine, a metal ion selected from calcium and iron, and at least one vitamin selected from vitamin A and vitamin D; wherein the solid oral dosage form reacts in simulated gastric fluid within 2 hours to generate molecular iodine with a ratio of molecular iodine to total iodine in the range of 0.8 to 1.0 by weight and repeating the ingesting step daily for at least 28 days and wherein the vitamin is physically separated from the source of iodine within the solid dosage form.

32. The method of claim 31, wherein the solid oral dosage form further comprises selenium.

33. The method of claim 31, wherein the solid oral dosage form further comprises an enteric coating that coats the vitamin A or vitamin D.

34. The method of claim 31, wherein the solid oral dosage form further comprises an ingredient selected from the group consisting of vitamin B1, gamma-linolenic acid, magnesium, and zinc.

35. The method of claim 31, wherein the solid oral dosage form comprises 6 to 50 milligrams of iodine.

36. A method for fabricating a solid dosage form comprising the steps of combining the following to form a combination
   (i) a source of iodine,
   (ii) a reactive agent,
   (iii) a metal ion selected from iron and calcium, and
   (iv) at least one vitamin selected from vitamin A and vitamin D, and
   fabricating a solid dosage form from the combination produced in the combining step,
   wherein the solid dosage form comprises
   (a) 0.2 to 20 mg iron or 10 to 500 mg of calcium, and
   (b) 3 to 60 mg of total iodine, and
   wherein the source of iodine and the reactive agent react together to produce 2.4 to 60 mg of molecular iodine when the solid dosage form is placed in simulated gastric fluid for a period of up to 2 hours, and
   wherein the vitamin is physically separated from the source of iodine within the solid dosage form.

37. The method of claim 36, wherein the iron or calcium is selected from the items listed in the iron or calcium rows of Table 1.

38. The method of claim 36, further comprising the step of selecting one or more additional ingredients from the group consisting of selenium, gamma-linolenic acid, vitamin B1, magnesium, and zinc and wherein the one or more additional ingredients are included in the combining step.

39. The method of claim 38, wherein the one or more added ingredients are selected from the items listed in Table 1.

40. The method of claim 38, further comprising the step of mixing the one or more added ingredients with an enteric coating.

41. The method of claim 36, wherein the solid oral dosage form comprises 6 to 50 milligrams of total iodine.

42. The solid oral dosage form of claim 1, wherein the solid oral dosage form comprises 20 to 100 mg of calcium.

43. The solid oral dosage form of claim 42, wherein the solid oral dosage form comprises greater than 6 milligrams and up to 40 milligrams of total iodine.

44. The solid oral dosage form of claim 1, wherein the solid oral dosage form comprises 9 to 30 milligrams of total iodine.

* * * * *